(12) United States Patent
Pei et al.

(10) Patent No.: US 8,536,121 B2
(45) Date of Patent: Sep. 17, 2013

(54) METHODS AND REAGENTS FOR THE DIAGNOSIS, PREVENTION AND TREATMENT OF INSULIN RESISTANCE USING BETA-ARRESTIN2 AND ITS UP-REGULATORS

(75) Inventors: Gang Pei, Shanghai (CN); Bing Luan, Shanghai (CN); Jian Zhao, Shanghai (CN)

(73) Assignee: Shanghai Institutes for Biological Sciences, CAS, Shanghai (CN)

( * ) Notice: Subject to any disclaimer, the term of this patent is extended or adjusted under 35 U.S.C. 154(b) by 0 days.

(21) Appl. No.: 13/132,750

(22) PCT Filed: Dec. 3, 2009

(86) PCT No.: PCT/CN2009/075275
§ 371 (c)(1),
(2), (4) Date: Jun. 3, 2011

(87) PCT Pub. No.: WO2010/063237
PCT Pub. Date: Jun. 10, 2010

(65) Prior Publication Data
US 2011/0245145 A1    Oct. 6, 2011

(30) Foreign Application Priority Data
Dec. 3, 2008 (CN) .......................... 2008 1 0203902

(51) Int. Cl.
*A61K 38/00* (2006.01)
*A01N 63/00* (2006.01)
*C12P 21/06* (2006.01)

(52) U.S. Cl.
USPC ............... 514/6.8; 514/6.9; 514/7.2; 514/7.3; 536/23.1; 424/93.1; 435/69.1

(58) Field of Classification Search
None
See application file for complete search history.

(56) References Cited

PUBLICATIONS

Verma, 1997, Nature, vol. 389, pp. 239-242.*
Kolchanov, 1988, Journal of Molecular Evolution, vol. 27, pp. 154-162.*
Pasquo, 2012, PLoS One, vol. 7, Issue 2, e32555.*
International Search Report w/translation from PCT/CN2009/075275 dated Mar. 18, 2010 (6 pages).
DeWire, Scott M. et al.; "b-Arrestins and Cell Signaling"; Annu. Rev. Physiol. 2007, 69:483-510 (31 pages).
Wang, Ping et al.; "b-Arrestin 2 Functions as a G-Protein-coupled Receptor-activated Regulator of Oncoprotein Mdm2"; The Journal of Biological Chemistry; 2003; vol. 278, No. 8; pp. 6363-6370 (8 pages).
Luan, Bing et al; "Deficiency of a b-arrestin-2 signal complex contributes to insulin resistance"; Nature, vol. 457; Feb. 26, 2009; pp. 1146-1150 (5 pages).
Extended European Search Report dated Jul. 6, 2012, from the European Patent Office for related European Patent Application No. 09830021.3 (6 pages).
Povsic, Thomas J., et al., "b-Arrestinl Mediates Insulin-like Growth Factor 1 (IGF-1) Activation of Phosphatidylinositol 3-Kinase (PI3K) and Anti-apoptosis", vol. 278, No. 51, Dec. 19, 2003; XP009160573, ISSN: 0021-9258; pp. 51334-51339.
Estall, Jennifer L., et al., "The GLP-2R as a Model for Incretin Receptor Signaling: The C-Terminus Modulates b-arrestin-2 Association, but Is Dispensable for Ligand-Induced Desensitization, Endocytosis and G-Protein-Dependent Effector Activation"; Database Biosis [Online], Biosciences Information Service; Database AccessionNo. PREV200600017218; XP009160659, 342-0R; vol. 54, No. Suppl. 1; Jun. 2005, ISSN: 0012-1797; p. A84.

* cited by examiner

*Primary Examiner* — Joanne Hama
*Assistant Examiner* — Ian Dang
(74) *Attorney, Agent, or Firm* — Osha Liang LLP

(57) ABSTRACT

The present invention provides the use of βarrestin2 protein or its up-regulators for manufacturing a composition for the prevention or treatment of insulin resistance or related disease in mammals. The reagents and the kits for the specific identification of βarrestin2 protein or its coding gene or transcript are also provided which can be used in diagnosis of insulin resistance or related diseases.

5 Claims, 12 Drawing Sheets

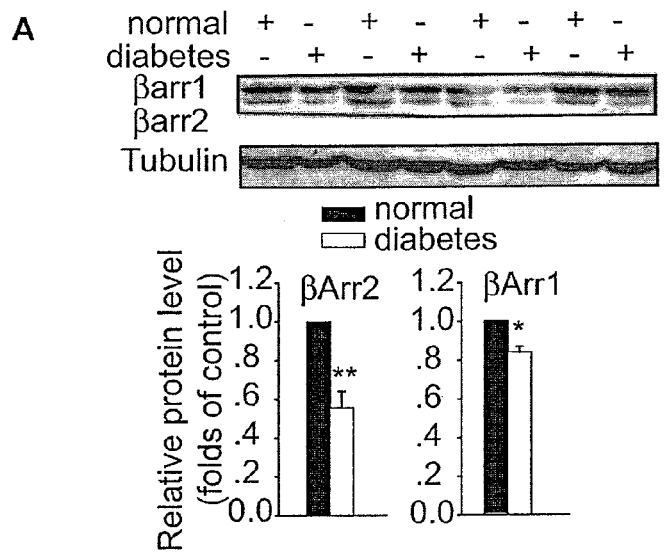

FIG. 8

| | pair1 | | pair2 | |
|---|---|---|---|---|
| | Patient1 | normal1 | patient2 | normal2 |
| Clinical features | | | | |
| Sex | Male | Male | Male | Male |
| Age | 61 | 60 | 66 | 63 |
| Biochemical features | | | | |
| Plasma glucose (mg/dl) | | | | |
| fasting | 173 | 95 | 205 | 103 |

| | pair3 | | pair4 | |
|---|---|---|---|---|
| | Patient3 | normal3 | patient4 | normal4 |
| Clinical features | | | | |
| Sex | Female | Female | Male | Male |
| Age | 75 | 70 | 50 | 53 |
| Biochemical features | | | | |
| Plasma glucose (mg/dl) | | | | |
| fasting | 152 | 91 | 155 | 103 |

| | pair5 | | pair6 | |
|---|---|---|---|---|
| | Patient5 | normal5 | patient6 | normal6 |
| Clinical features | | | | |
| Sex | Male | Male | Male | Male |
| Age | 57 | 53 | 50 | 53 |
| Biochemical features | | | | |
| Plasma glucose (mg/dl) | | | | |
| fasting | 152 | 98 | 155 | 103 |

| | pair7 | | pair8 | |
|---|---|---|---|---|
| | Patient7 | normal7 | patient8 | normal8 |
| Clinical features | | | | |
| Sex | Male | Male | Female | Female |
| Age | 60 | 60 | 53 | 50 |
| Biochemical features | | | | |
| Plasma glucose (mg/dl) | | | | |
| fasting | 170 | 96 | 195 | 75 |

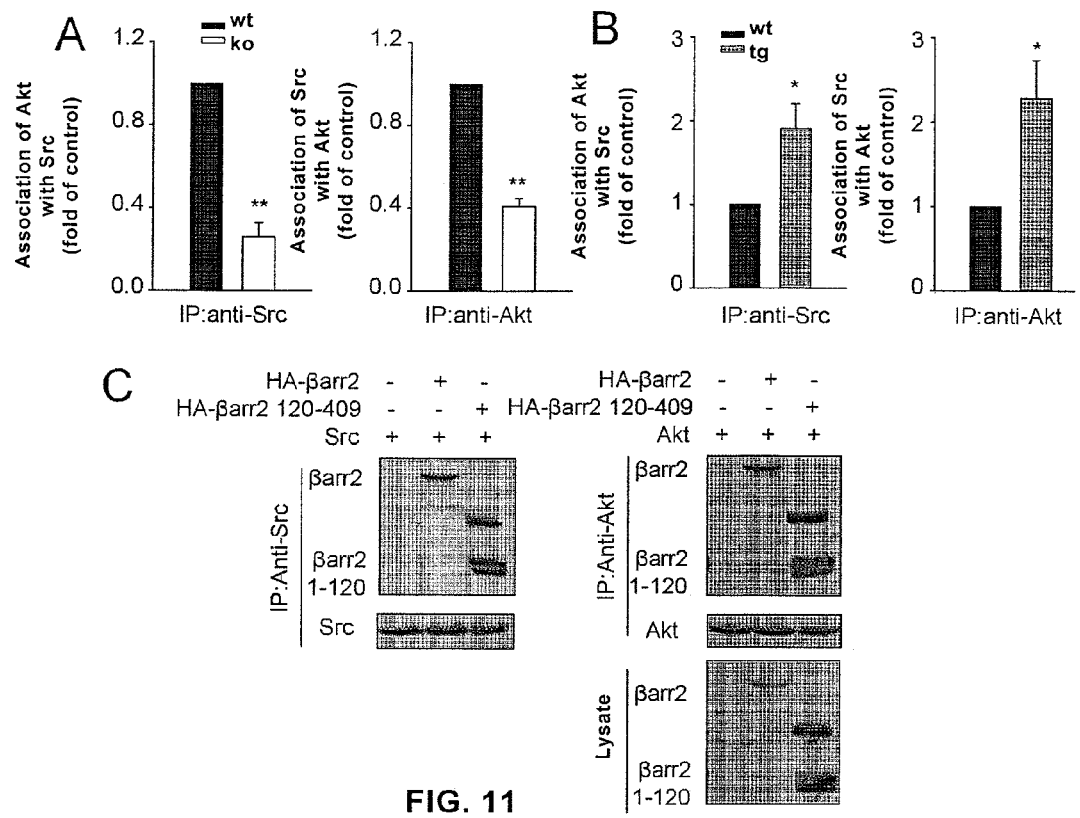
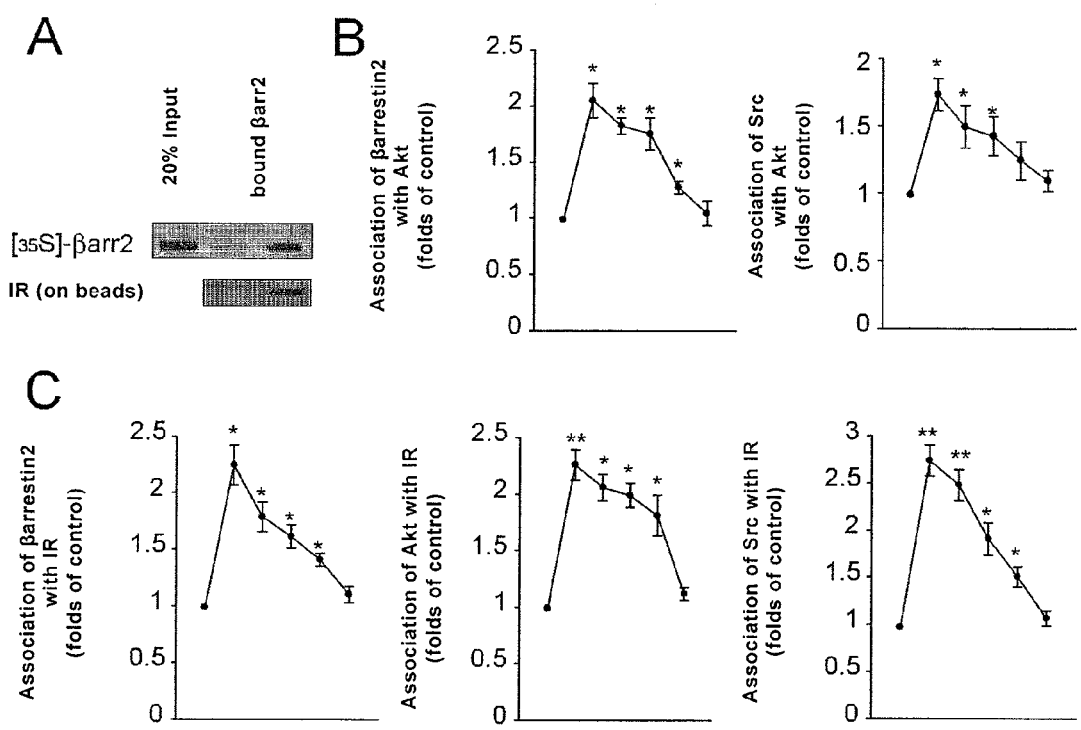
FIG. 12

SEQUENCE LISTING

<160> NUMBER OF SEQ ID NOS: 6

<210> SEQ ID NO 1
<211> LENGTH: 21
<212> TYPE: DNA
<213> ORGANISM: artificial sequence
<220> FEATURE:
<223> OTHER INFORMATION: primer

<400> SEQUENCE: 1
aagggacacg agtgttcaag a                                                  21

<210> SEQ ID NO 2
<211> LENGTH: 19
<212> TYPE: DNA
<213> ORGANISM: artificial sequence
<220> FEATURE:
<223> OTHER INFORMATION: primer

<400> SEQUENCE: 2
cccgctttcc caggtagac                                                     19

<210> SEQ ID NO 3
<211> LENGTH: 19
<212> TYPE: DNA
<213> ORGANISM: artificial sequence
<220> FEATURE:
<223> OTHER INFORMATION: primer

<400> SEQUENCE: 3
ggcaagcgcg actttgtag                                                     19

<210> SEQ ID NO 4
<211> LENGTH: 21
<212> TYPE: DNA
<213> ORGANISM: artificial sequence
<220> FEATURE:
<223> OTHER INFORMATION: primer

<400> SEQUENCE: 4
gtgagggtca cgaacactttt c                                                 21

<210> SEQ ID NO 5
<211> LENGTH: 25
<212> TYPE: DNA
<213> ORGANISM: artificial sequence
<220> FEATURE:
<223> OTHER INFORMATION: primer

<400> SEQUENCE: 5
cctgctggat tacattaaag cactg                                              25

<210> SEQ ID NO 6
<211> LENGTH: 21
<212> TYPE: DNA
<213> ORGANISM: artificial sequence
<220> FEATURE:
<223> OTHER INFORMATION: primer

<400> SEQUENCE: 6
ttcaacactt cgagaggtcc t                                                  21

METHODS AND REAGENTS FOR THE DIAGNOSIS, PREVENTION AND TREATMENT OF INSULIN RESISTANCE USING BETA-ARRESTIN2 AND ITS UP-REGULATORS

BACKGROUND OF INVENTION

1. Field of the Invention

The invention relates generally to treatments of insulin resistance. More specifically, it relates to βarrestin2 protein and its roles in insulin sensitivity. The invention also relates to methods and reagents for diagnosing, preventing, and treating diseases or conditions associated with insulin resistance.

2. Background Art

Insulin resistance (or insulin insensitivity) has become one of the most serious public health threats in recent years. It leads to deregulation of glucose homeostasis and is associated with glucose intolerance, obesity, dyslipidemia, hypertension and cardiovascular disorder. As a compensatory response, body produces more insulin, leading to higher levels of blood insulin (hyperinsulinaemia). As the syndrome progresses, this eventually leads to diabetes.

Insulin resistance refers to a decreased capacity of circulating insulin to regulate glucose and lipid metabolism in adipose tissue, liver, and skeletal muscle, due to diminished insulin receptor (IR) response to insulin stimulation. Under normal conditions, insulin in circulation is recognized by IR on the cell surfaces of adipose tissue, liver, or skeletal muscle. After IR is stimulated by insulin, it phosphorylates insulin receptor substrate proteins (IRS proteins). Phosphorylation of IRS proteins in turn leads to the activation of the phosphatidylinositol 3-kinase (PI3K) signaling pathway. The PI3K signaling pathway then mediates major metabolic actions of insulin.

Insulin signaling is a complex and highly regulated signaling networks. In the insulin signaling pathway, PI3K phosphorylates phosphatidylinositol-4,5-bisphosphate (PI4,5-$P_2$) to produce phosphatidylinositol-3,4,5-trisphosphate (PI3,4,5-$P_3$), which serves as a membrane anchor for Akt and PDKs (phosphoinositide-dependent protein kinases). Upon translocation to the membrane, Akt is phosphorylated by PDKs and becomes activated. Activated Akt in turn phosphorylates downstream kinases and transcription factors, thereby mediating most of the metabolic actions of insulin.

Defect at any critical nodes in the insulin signaling pathway (for example, defects in the activity of Ark) can result in insulin resistance. It has been shown that knockout of Akt (Cho, H. et al., "*Insulin resistance and a diabetes mellitus-like syndrome in mice lacking the protein kinase Akt2 (PKB beta)*," Science, 292, 1728-31, 2001) or expression of Akt kinase-deficient mutants (Takata, M. et al., "*Requirement for Akt (protein kinase B) in insulin-induced activation of glycogen synthase and phosphorylation of 4E-BP1 (PHAS-1)*," J. Biol. Chem., 274, 20611-8, 1999) leads to insulin resistance. Even dysregulation of proteins that regulate Akt activity (such as, phosphatase-2A (PP2A) or tribbles-3 (TRB3)) can contribute to insulin resistance, demonstrating the pivotal role of Akt in insulin signaling. See, Resjo, S. et al., "*Protein phosphatase 2A is the main phosphatase involved in the regulation of protein kinase B in rat adipocytes*," Cell Signal, 14, 231-8, 2002; and Du, K. et al., "*TRB3: a tribbles homolog that inhibits Akt/PKB activation by insulin in liver*," Science, 300, 1574-7, 2003.

Because insulin resistance usually develops before the occurrence of subsequent abnormalities (e.g., type II diabetes, glucose intolerance, obesity, dyslipidemia, hypertension, cardiovascular disorder, hyperuricemia, and hyperinsulinaemia), identifying biomarkers for insulin resistance would provide new approaches to preventing and/or treating insulin resistant patients.

SUMMARY OF INVENTION

Restoring βarrestin2 expression levels or its activity is useful in the prevention or treatment of insulin resistance or insulin resistance-associated diseases, such as type II diabetes, glucose intolerance, obesity, dyslipidemia, hypertension, cardiovascular disorder, hyperuricemia, and hyperinsulinaemia.

The first aspect in accordance with the present invention provides use of 1 arrestin2 proteins or their up-regulators (such as agents that increase βarrestin2 expression levels (expression up-regulators) in target tissues) in the manufacture of compositions for preventing or treating insulin resistance or insulin resistance-associated diseases in mammals.

In another preferred embodiment, in which insulin resistance or insulin resistance-associated diseases are selected from: type II diabetes, hypertension, dyslipidemia, cardiovascular disorder, obesity, hyperinsulinaemia, hyperuricemia, or glucose intolerance.

In another preferred embodiment, in which up-regulators of βarrestin2 protein include expression vectors containing polynucleotides encoding βarrestin2.

In another preferred embodiment, in which expression vectors are plasmid vectors.

In another preferred embodiment, in which expression vectors are viral vectors.

In another preferred embodiment, in which viral vectors are selected from the following group: retrovirus, adenovirus, herpes virus, vaccinia virus or adeno-associated virus.

In another preferred embodiment, in which mammals are human.

Another aspect of the present invention provides uses of βarrestin2 proteins for the manufacture of reagents for diagnosing insulin resistance or insulin resistance-associated diseases.

Another aspect of the present invention provides uses of reagents that specifically identify βarrestin2 proteins, their coding genes, or transcripts for the manufacture of test kits for diagnosing insulin resistance or insulin resistance-associated diseases.

In another preferred embodiment, in which reagents that specifically identify βarrestin2 proteins, their coding genes, or transcripts are selected from: specific anti-βarrestin2 antibodies; or primers specifically amplifying βarrestin2 mRNA.

Another aspect of the present invention provides a method for diagnosing insulin resistance, includes:

Analyzing βarrestin2 expression levels in test samples, comparing with βarrestin2 expression levels in normal samples, when βarrestin2 expression levels in test samples are comparatively lower, indicating insulin resistance in test subjects.

In another preferred embodiment, in which analyzing βarrestin2 expression levels in test samples is determining protein expression levels by using βarrestin2 antibodies.

In another preferred embodiment, in which analyzing βarrestin2 expression levels in test samples is determining mRNA expression levels by using reverse transcription PCR primers.

Another aspect of the present invention provides a method for preventing or treating insulin resistance or insulin resistance-associated diseases, includes administering to mammals therapeutically effective amount of reagents that can increase βarrestin2 expression levels in target tissues.

Another aspect of the present invention provides a diagnosis test kit for diagnosing insulin resistance or insulin resistance-associated diseases, test kit contains: reagents that specifically identify βarrestin2 proteins or their coding genes or transcripts.

In another preferred embodiment, in which reagents that specifically identify
βarrestin2 proteins or their coding genes or transcripts are selected from: specific anti-βarrestin2 protein antibodies, or one or more pairs of reverse transcription PCR primers that specifically amplify βarrestin2 mRNA.

Another aspect of the present invention provides a use of βarrestin2 proteins or their up-regulators for the manufacture of compositions for inducing formation of insulin receptor (IR)/Akt/βarrestin2/Src signal transduction complexes.

Another preferred embodiment provides a signal transduction complex (preferably isolated complex), in which complex includes: insulin receptors, Akt, βarrestin2 and Src.

Another preferred embodiment provides use of signal transduction complex for screening materials that prevent or treat insulin resistance or insulin resistance-associated diseases in mammals. The present invention provides a new method for diagnosing insulin resistance. Analyzing βarrestin2 expression levels in test samples, and comparing with βarrestin2 expression levels in test samples and in normal samples to diagnose the levels of insulin resistance; comparatively lower βarrestin2 expression levels indicates the presence of insulin resistance.

Another aspect of the present invention relates to a new method for preventing or treating insulin resistance or insulin resistance-associated diseases. In one embodiment of the present invention, said method includes administering to mammals therapeutically effective amount of reagents that can increase βarrestin2 expression levels in specific tissues.

Another aspect of the present invention relates to diagnosis test kit for diagnosing insulin resistance. In one embodiment of the present invention, said test kit contains antibodies that identify βarrestin2 proteins or one or more RT-PCR primers that amplify βarrestin2 mRNA.

Other aspects and advantages of the invention will be apparent from the following description and the appended claims.

BRIEF DESCRIPTION OF DRAWINGS

FIG. 1A, Representative immunoblots of βarrestin protein levels in adipose tissue, liver, and skeletal muscle of lean (n=5) and db/db mice (n=5). The results shown are from densitometry analysis. FIG. 1B, βarrestin2 mRNA levels were examined by quantitative RT-PCR in adipose tissue, liver, and skeletal muscle of lean (n=5) and db/db mice (n=5). Lean mice were 8-weeks old and fed with a regular diet (body weight 20.3±1.2 g, food intake 3.5±0.5 g), db/db mice were 8-weeks old fed with a regular diet (body weight 38.5±1.4 g, food intake 4.8±0.7 g). FIG. 1C, Representative immunoblots of βarrestin in adipose tissue, liver, and skeletal muscle of C57BL/6 mice fed with a regular diet (RD) (body weight 22.6±2.1 g, food intake 3.6±0.3 g) (n=5) or high-fat diet (HFD) (body weight 36.7±1.9 g, food intake 4.1±0.2 g) (n=5). Densitometry analysis was shown. FIG. 1D, βarrestin2 mRNA levels in adipose tissue, liver, and skeletal muscle of C57BL/6 mice fed with a regular diet (RD) (n=5) or high-fat diet (HFD) (n=5) for 8 weeks. 6-weeks old C57BL/6 mice were fed on RD or HFD for an additional 8 weeks. Data are presented as mean ±s.e.m. *P<0.05, **P<0.005, versus control.

FIG. 3G, Blood glucose concentration of db/db mice (n=8) injected with adenovirus encoding either βGal or βarrestin2. GTTs (1.5 g·kg$^{-1}$) (FIG. 3H), ITTs (1.5 U·kg$^{-1}$) (FIG. 3I) and AUC glucose levels (FIG. 3J) in db/db mice at 7 days after virus injection. For HFD, 6-weeks old mice were fed on HFD for an additional 8 weeks. db/db mice were 8-weeks old when receiving adenovirus injection. Data are presented as mean ±s.e.m. *P<0.05, **P<0.005, versus control.

FIG. 4A, Activation of PI3K by insulin in livers of βarr2-ko mice (n=6), βarr2-tg mice (n=6) and their wild type littermates (n=6). Mice were injected with either saline or insulin (1 U·kg$^{-1}$) for 10 min. PI3K were immuno-purified from liver extracts and PI3K activity were measured by ELISA. Data are presented as mean ±s.e.m. *P<0.05, **P<0.005, versus control. FIG. 4B, FIG. 4C, Activation of Akt and downstream targets by insulin in livers of βarr2-ko mice (n=6) (FIG. 4B), βarr2-tg mice (n=6) (FIG. 4C) and their wild type littermates (n=6). Liver protein extracts prepared as in A were used for immunoblot analysis of pAkt, pFoxo1, and pGSK3. FIG. 4D, Activation of Akt and downstream targets by insulin in livers of db/db mice injected with adenovirus encoding either βGal or βarrestin2 for 7 days. FIG. 4E, Src-dependent activation of Akt. Hep3B hepatocytes were treated with or without 10 μM Src inhibitor PP2 or 100 nM PI3K inhibitor Wortmanin for 30 min, and then stimulated by 100 nM insulin. Phosphorylation levels of Akt at serine/threonine or tyrosine (n=6) were shown. FIG. 4F, Tyrosine phosphorylation of Akt induced by insulin in livers of βarr2-ko mice (n=6), βarr2-tg mice (n=6) and their wild type littermates (n=6). Akt immuno-purified from protein extracts made in FIG. 4B and FIG. 4C was subjected to immunoblot using antibodies against phosphorylated tyrosine. All mice were 8-weeks old fed with a regular diet. Data are presented as mean ±s.e.m. *P<0.05, **P<0.005, versus control.

FIG. 5A, Interactions of Akt/βarrestin2/Src were assayed by immunoprecipitation of lysate form liver of C57BL/6 mice (n=5). FIG. 5B, Interaction of Akt and Src in liver of wild type littermates but not βarr2-ko mice. Liver protein extracts from βarr2-ko mice (n=6) and their wild type littermates (n=6) were used for immunoprecipitation by anti- Akt or anti-Src antibodies. FIG. 5C, Enhanced interaction of Akt and Src in liver of βarr2-tg mice. Liver protein extracts from βarr2-tg mice (n=6) and their wild type littermates (n=6) were used for immunoprecipitation by anti-Akt or anti-Src antibodies. FIG. 5D, Diagram showing truncation mutants of βarrestin2 and their interaction feature with Akt or Src. FIG. 5E, βarresti2 1-185 interacts with Src but not Akt. HA-βarrestin2 that co-immunoprecipitated from Hep3B hepatocytes overexpressing Akt or Src without or with HA-βarrestin2, HA-βarrestin2 1-185 was shown on immunoblots using anti-HA antibodies (n=3). FIG. 5F, Hep3B hepatocytes overexpressing HA-βarrestin2 1-185 or βGal were subjected to immunoprecipitation using anti-Akt antibodies. Akt, Src in the immunopurified complex were shown on immunoblots (n=3). FIG. 5G, βarrestin2 1-185 inhibits activation of Aid and downstream targets by insulin-treatment. Hep3B hepatocytes overexpressing HA-βarrestin2 1-185 or βGal were stimulated by insulin and then subjected to immunoblot analysis of pAkt, pFoxol, and pGSK3. All mice were 8-weeks old fed with a regular diet.

FIG. 6A, Insulin induces formation of Akt/βarrestin2/Src complex in vivo. C57BL/6 mice (n=6) were injected with 1 U·kg$^{-1}$ insulin for the indicated times, and liver protein extracts were prepared for immunoprecipitation using anti-Akt antibodies. Akt, βarrestin2 and Src in the immunopurified complex were shown on immunoblots. FIG. 6B, Insulin stimulated interaction of Akt/βarrestin2/Src with IR. Liver protein extracts prepared as described in a were subjected to immunoprecipitation for IRβ. Akt, βarrestin2 and Src associated with IRβ were detected on immunoblots (n=6). FIG. 6C, βarrestin2 is essential for association of Akt/Src with the IR. Liver protein extracts prepared from βarr2-ko (n=6), βarr2-tg (n=6), their wild type littermates (n=6) as described were subjected to immunoprecipitation for IRβ. Akt and Src associated with IRβ were detected on immunoblots. FIG. 6D, βarrestin2 186-409 interacts with IRβ, but not Akt or Src. Hep3B hepatocytes overexpressing HA-βarrestin2, HA-βarrestin2 186-409 or βGal are lysed and indicated protein were immunoprecipitated using respective antibodies, HA-tagged βarrestin2 that in the precipitates were shown (n=3). FIG. 6E, βarrestin2 186-409 inhibits activation of Akt and downstream targets by insulin-treatment. Hep3B hepatocytes overexpressing HA-βarrestin2 186-409 or βGal were subjected for immunoblot analysis of pAkt, pFoxol, and pGSK3. All mice were 8-weeks old fed with a regular diet.

FIG. 7A, Blood glucose concentration of C57BL/6 mice (n=8) at indicated days after injection with adenovirus encoding βGal, βarrestin2 1-185 or βarrestin2 186-409. GTTs (1g·kg$^{-1}$) (FIG. 7B), ITTs (1 U·kg$^{-1}$) (FIG. 7C) and AUC glucose levels (FIG. 7D) in C57BL/6 mice at 7 days after injection with adenovirus encoding βGal, βarrestin2 1-185 or βarrestin2 186-409. C57BL/6 mice were 8-weeks old fed on regular diet (RD). Data are presented as mean ±s.e.m. *P<0.05, **P<0.005, versus control. FIG. 7E, Schematic representation of IR/Akt/βarrestin2/Src signal complex formed following insulin-stimulation.

FIGS. 8A-B show downregulation of βarrestin½ in clinic sample of type 2 diabetes. FIG. 8A, Representative immunoblots of βarrestin½ in liver of individual clinical samples (upper). Samples are paired by age. Lower panel: densitometry analysis of βarrestin½ protein levels in liver of clinical samples (n=8). FIG. 8B, Clinical, biochemical characteristics of the subjects used in FIG. 8A. Data are presented as mean ±s.e.m. *P<0.05, **P<0.005, versus control.

FIG. 9A, FIG. 9B, Body weight and food intake of βarr2-ko mice (n=10), βarr2-tg mice (n=10) and their wild type littermates (n=10) fed on regular diet. Expression of βarrestins was shown. FIG. 9C, Plasma insulin concentrations during GTTs (1 g·kg–1) in βarr2-ko mice (n=10), βarr2-tg mice (n=11) and wild type littermates (n=8). FIG. 9D, FIG. 9E, Body weight and food intake of βarr2-ko mice (n=8), βarr2-tg mice (n=8) and their wild type littermates (n=8) fed on high-fat diet. FIG. 9F, FIG. 9G, Body weight and food intake of db/db mice injected with adenovirus encoding gal (n=8) or βarrestin2 (n=8) fed on regular diet. Expression of βarrestins was shown. FIG. 9H, White adipose tissue (perigonadal; WAT) weight of βarr2-ko mice (n=6), βarr2-tg mice (n=6) and their wild type littermates (n=6) fed on regular diet under fed conditions. FIG. 9I, Adipocyte size in WAT of βarr2-ko mice (n=6), βarr2-tg mice (n=6) and their wild type littermates (n=6) fed on regular diet was determined by H&E staining under fed conditions. FIG. 9J, Plasma free fatty acid (FFA), triglyceride as well as cholesterol levels of βarr2-ko mice (n=6), βarr2-tg mice (n=6) and their wild type littermates (n=6) fed on regular diet under fasted conditions. FIG. 9K, G6p and pepck mRNA levels were assayed by quantitative RT-PCR in liver sample of βarr2-ko mice (n=5), βarr2-tg mice (n=5) and their wild type littermates (n=5) fed on regular diet under fasted conditions. FIG. 9L, Glucose production treated with or without 10 nM insulin for 3h in primary hepatocytes from βarr2-ko mice (n=6), βarr2-tg mice (n=6) and their wild type littermates (n=6) fed on regular diet. FIG. 9M, Ex vivo glucose uptake in soleus muscle isolated from βarr2-ko mice (n=6), βarr2-tg mice (n=6) and their wild type littermates (n=6) fed on regular diet. βarr2-ko mice, βarr2-tg mice and their wild type littermates were 8-weeks old. Data are presented as mean ±s.e.m. *P<0.05, **P<0.005, versus control.

FIG. 10A, In vitro Akt kinase assay using immunoprecipitated Akt from βarr2-ko mice, βarr2-tg mice and their wild type littermates. 8-week-old βarr2-ko mice (n=4), βarr2-tg mice (n=4) and their wild type littermates (n=4) fed on regular diet were injected with either saline or insulin for 10 min after fasting for 6h. Liver protein extracts were prepared for immunoprecipitation of Akt, and in vitro kinase assay was conducted. FIG. 10B, Densitometry analysis of FIG. 4B, and 4C. FIG. 10C, Densitometry analysis of FIG. 4D. FIG. 10D, Densitometry analysis of FIG. 4F. FIG. 10E, Akt Tyr315/326Ala showed decreased activity under insulin stimulation. Hep3B hepatocytes expressed with flag-Akt or flag-Akt 2M (Tyr315/326A1a) were subjected to immunoprecipitation with anti-flag antibody and followed by immunoblot with anti-pTyr, anti-pAkt (ser473), and anti-flag antibodies (n=3). FIG. 10F, Activation of Akt by insulin in skeletal muscle of βarr2-ko mice (n=6), βarr2-tg mice (n=6), and their wild type littermates (n=6). Skeletal muscle protein extracts from 8-week-old βarr2-ko mice (left), βarr2-tg mice (right) and their wild type littermates injected with either saline or insulin for 10 min were prepared for immunoblot analysis of total Akt, and active Akt (p-Thr308, p-Ser473). FIG. 10G, Densitometry analysis of active Akt (p-Thr308, p-Ser473) levels in F. Data are presented as mean s.e.m. *P <0.05, **P<0.005, versus control.

FIGS. 11A-C show βarrestin2 scaffolded Akt/Src interaction. FIG. 11A, Densitometry analysis of FIG. 5B. FIG. 11B, Densitometry analysis of FIG. 5C. FIG. 11C, Representative immunoblots of βarrestin2 120-409 interaction with Src and Akt in Hep3B hepatocytes (n=4). Data are presented as mean ±s.e.m. *P<0.05, **P<0.005, versus control.

FIG. 12A, Direct interaction of βarrestin2 and IR. In vitro pull down assay was done using in vitro transcribed and translated [$^{35}$S]-βarrestin2 and IR immunoprecipitated from Hep3B hepatocytes. FIG. 12B-FIG. 12C, Densitometry analysis of FIG. 6A-B. FIG. 12D, Wortmannin treatment inhibits βarrestin2 scaffolded Akt/Src interaction. Hep3B hepatocytes were treated with or without 100 nM Wortmannin for 30 min, and then stimulated by 100nM insulin for 10 min. Immunoprecipitation by anti-IR or anti-Src followed by immunoblot with specific antibodies as indicated. Representative immunoblot was shown (n=3). FIG. 12E, Densitometry analysis of FIG. 6C. Data are presented as mean ±s.e.m. *P<0.05, **P<0.005, versus control.

FIG. 13A, Blood glucose concentration of db/db mice (n=8) at indicated days after injection with adenovirus encoding βGal, βarrestin2 1-185 or βarrestin2 186-409. GTTs (1.5 g·kg−1) (FIG. 13B), ITTs (1.5 U·kg−1) (FIG. 13C) and AUC glucose levels (FIG. 13D) in db/db mice at 7 days after injection with adenovirus encoding βGal, βarrestin2 1-185 or βarrestin2 186-409. db/db mice were 8-weeksold fed with a regular diet. Data are presented as mean ±s.e.m. *P<0.05, **P<0.005, versus control.

DETAILED DESCRIPTION

Figure 1:
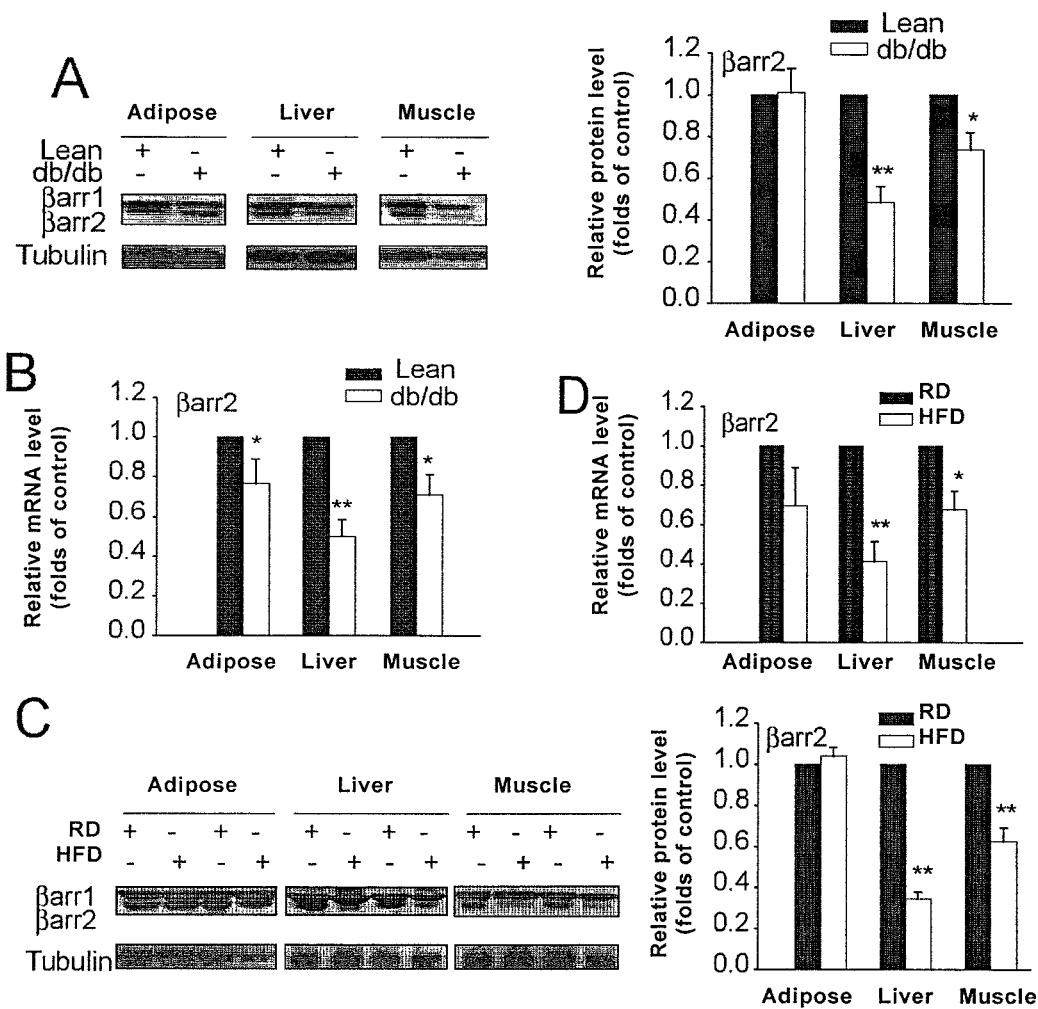
FIGS. 1A-D show apparent downregulation of βarrestin2 in samples of type 2 diabetic mice.

Embodiments of the invention relate to diagnosis, prevention, and treatment of insulin resistance. Because insulin resistance develops before any subsequent symptoms show up, being able to predict, prevent or control insulin resistance would confer great benefits by allowing early intervention to prevent the development of any symptoms. The invention is based on inventors' unexpected discovery that βarrestin-2 plays an important role in insulin signaling.

Arrestins are a family of proteins important for the regulation of signal transductions mediated by G-protein coupled receptors (GPCRs) within cells. G-protein coupled receptors (GPCRs) form the largest family of cell receptors and are involved in a wide range of cellular functions. Arrestins participate in the regulation of GPCR activities.

Upon agonist binding, GPCRs are activated and recruit heterotrimeric G-proteins to transduce the signals. Once these receptors are activated, they will need to be turned off or they will need to adapt to a constant stimulus, i.e., the activated receptors need to be silenced or dampened. The silencing mechanism involves phosphorylation by G protein-coupled receptor kinases (GRKs). This phosphorylation marks the activated receptors for arrestin binding. Once arrestins are bound to the activated receptors, the receptors cannot signal any further. Thus, arrestins play an important role in the agonist-mediated desensitization of GPCRs, and they cause specific dampening of cellular responses to stimuli, such as hormones, neurotransmitters, or sensory signals.

In addition to their abilities to arrest signal transduction of GPCRs, arrestins have also been found to participate in specific functions of other types of receptors (non-GPCRs). With these other receptors, arrestins can directly participate in their signaling pathways by functioning as adaptor molecules. Specifically, arrestins form signaling complexes with the activated receptors. Once in the complexes, arrestins function as adaptor proteins to link the activated receptors with distinct sets of accessory and/or effector proteins. Being the linkers, arrestins determine the specificity, efficiency, and capacity of signals, as well as the intracellular movement of the activated receptors.

For example, upon stimulation of β$_2$AR or the Neurokinin 1 (NK-1) receptor for substance P, βarrestin1 or βarrestin2 binds to these activated receptors. Once bound to the activated β$_2$AR or NK-1 receptor, βarrestin1 or βarrestin2 recruits Src and downstream kinases (ERK1/2) to the activated receptor to form complexes. See, DeFea, K. A. et al., "*The proliferative and antiapoptotic effects of substance P are facilitated by formation of a beta-arrestin-dependent scaffolding complex,*" Proc. Natl. Acad. Sci. U.S.A., 97, 11086-91, 2000; and Luttrell, L. M. et al., "Beta-arrestin-dependent formation of beta2 adrenergic receptor-Src protein kinase complexes," Science, 283, 655-61, 1999. Similarly, signaling complexes that contain proteins in the activated ERK cascade (e.g., Raf, MEK and ERK) or JNK cascade (e.g., ASK1, MKK4 and JNK3) are also scaffolded by βarrestin1/2, following stimulation of angiotensin II type 1A receptor (AT1aR). See, Luttrell, L. M. et al., "*Activation and targeting of extracellular signal-regulated kinases by beta-arrestin scaffolds,*" Proc. Natl. Acad. Sci. U.S.A., 98, 2449-54, 2001; and McDonald, P. H. et al., "*Beta-arrestin 2: a receptor-regulated MAPK scaffold for the activation of JNK*3," Science, 290, 1574-7, 2000. Studies have shown that these βarrestin-mediated signaling complexes are essential for receptor signaling and biological functions of the cells.

While bindings of arrestins with several non-GPCRs have been demonstrated, there has been no evidence that arrestins can bind with the insulin receptor, which is not a GPCR. Embodiments of the invention are based on the unexpected findings that βarrestin2 protein not only binds to the insulin receptor (IR), but also functions as an indispensable scaffold molecule in the insulin receptor (IR) signaling pathway. Specifically, inventors of the present invention have found that βarrestin2 links Akt and Src to insulin receptor (IR) following insulin-stimulation. In addition, the inventors found that proper formation of the IR/Akt/βarrestin2/Src signal complex is critical for insulin signaling and downstream metabolic actions.

For example, inventors of the present invention found that down-regulation or mutation of βarrestin2 disrupts insulin signaling and aggravates insulin resistance. The inventors also found that βarrestin2-dependent signaling complexes are intrinsically involved in IR signaling and that βarrestin2 dysfunction contributes to the development of insulin resistance and progression of type 2 diabetes. These findings suggest that βarrestin-2 may be a useful target for the diagnosis and management of disorders associated with insulin resistance, such as type II diabetes, hypertension, dyslipidemia, cardiovascular disease, obesity, and other abnormalities including hyperuricemia. The following describes the various findings in details.

βarrestin2 used in the present invention may be those exist in nature, such as those isolated or purified from mammals. In addition, βarrestin2 proteins may be prepared artificially, such as recombinant βarrestin2 proteins produced by conventional genetic engineering recombination technology. Preferably, the present invention may use recombinant βarrestin2 proteins.

Any suitable βarrestin2 proteins may be used in the present invention. βarrestin2 proteins include full-length βarrestin2 protein or biologically active fragments (or referred to as active fragments). For example, amino acid sequence of βarrestin2 proteins may be essentially the same as the sequence of GenBank number: NM145429.

The present invention also includes amino acid sequence of βarrestin2 protein having one or more amino acid residue substitutions, deletions, or insertions. βarrestin2 proteins or their biologically active fragments include a portion of sequence having conserved amino acid substitutions, amino acid substitutions may not affect activity or may maintain partial activity. Suitable amino acid substitutions are techniques commonly known in the art, these techniques can be easily performed, and ensuring obtained molecules would not change biological activity. Generally speaking, one skilled in the art would know that a single amino acid change within non-essential area of polypeptide basically would not change biological activity. See Watson et al., Molecular Biology of The Gene, 4$^{th}$ edition, 1987, The Benjamin/Cummings Pub. Co. P224.

Any biologically active βarrestin2 protein fragments may be used in the present invention. Herein, biologically active βarrestin2 protein fragment mean a polypeptide, which still maintains whole or partial activity of full-length βarrestin2 protein. Under normal conditions, biologically active fragments maintain at least 50% activity of full-length βarrestin2 protein. Under more preferable conditions, active fragments maintain 60%, 70%, 80%, 90%, 95%, 99%, or 100% activity of full-length βarrestin2 protein.

Modified or improved βarrestin2 proteins can also be used in the present invention, for example, modified or improved βarrestin2 proteins, whose half-life, functionality, metabolism, and/or protein activity has been enhanced. Modified or improved βarrestin2 proteins may have smaller similarity with naturally existed βarrestin2 proteins, but also can prevent or treat insulin resistance in mammals, but may not have other adverse effects or toxicity. In other words, any type of alteration, which does not affect biological activity of βarrestin2 proteins, may be used in the present invention.

The present invention also includes isolated nucleotides that encode biologically active βarrestin2 protein fragments, and their complementary sequences. Entire DNA sequences that encode biologically active fragments of βarrestin2 proteins may be synthesized artificially, or obtained by PCR amplification methods. After obtaining DNA sequences encoding biologically active fragments of βarrestin2 proteins, ligate them to suitable expression vectors, and then transfer to suitable host cells. Finally, through culturing transformed host cells, and obtain proteins by isolation and purification.

The present invention also includes vectors that contain nucleotides encoding biologically active fragments of βarrestin2 proteins. Vectors may also contain expression regulatory sequences operably linked to nucleotide sequences for protein expression. "Operably linked" or "capable of operably linked to" means a condition that certain parts of linear DNA sequences can regulate or control activity of the rest of same linear DNA sequences. For example, if promoter controls transcription of sequences, then it is capable of operably linked to encoding sequences. Expression vectors, for example, can be a kind of viral vectors. Viral vectors may be selected from the following group: retrovirus, adenovirus, herpes virus, vaccinia virus or adeno-associated virus. Preferred viral vectors are adenoviral vectors.

The present invention also includes up-regulators of βarrestin2 proteins, through up-regulating expression or activity of βarrestin2 proteins, resulting in effects of preventing and treating insulin resistance or insulin resistance-associated diseases. As used in the present disclosure, up-regulators include stimulators, inducers, etc. Any materials, which can increase βarrestin2 protein activity, maintain βarrestin2 protein stability, promote βarrestin2 protein expression, prolong βarrestin2 protein effective action time, or enhance βarrestin2 transcription and translation, may be used in the present invention, and serving as materials for preventing and treating insulin resistance or insulin resistance-associated diseases.

Based on inventors' new findings as described above, βarrestin2 can also be used as indicator for diagnosing insulin resistance or insulin resistance-associated diseases: (i) conducting analysis on classification, identification, diagnosis, and/or susceptibility of insulin resistance or insulin resistance-associated diseases; (ii) evaluating pharmaceutical compositions, effects of pharmaceutical compositions, after cure, and selection of suitable treatment methods of insulin resistance or insulin resistance-associated diseases among related people groups; (iii) early evaluating risk of getting insulin resistance or insulin resistance-associated diseases among related people groups and early detection and prevention. For example, by isolating people with insulin resistance or insulin resistance-associated diseases due to abnormal βarrestin2 gene expression, they can be specifically treated.

Thus, βarrestin2 proteins can be used to manufacture reagents for diagnosing insulin resistance or insulin resistance-associated diseases, reagents are, for example, those that specifically identify or bind βarrestin2 proteins, such as using βarrestin2 proteins to generate a series of antibodies, and selecting from these antibodies that have excellent binding specificity suitable for clinical diagnosis.

Thus, the present invention also provides use of reagents for specific identification of βarrestin2 proteins or their coding genes or transcripts, use for manufacturing test kits for diagnosing insulin resistance or insulin resistance-associated diseases.

Techniques that employ various techniques known in the art to determine whether or not βarrestin2 gene or transcript is present and expression levels are included in the present invention. For example, using previously known techniques, such as Southern blot methods, Western blot methods, DNA sequence analysis, PCR, etc., these methods can be used in combination.

The present invention also provides reagents for determining whether or not βarrestin2 gene or transcripts are present and their expression levels in samples. Preferably, when determining gene levels, primers that specifically amplify βarrestin2 may be used; or using specific βarrestin2 probes to determine whether or not βarrestin2 gene is present; when determining protein levels, antibodies or partners that specifically bind βarrestin2 proteins can be used to determine βarrestin2 protein expression levels. More preferably, reagents that determine βarrestin2 transcription levels or expression levels are selected from: specific anti-βarrestin2 antibodies; or primers that specifically amplify βarrestin2 mRNA.

As preferred embodiment of the present invention, reagents are primers, capable of specifically amplifying βarrestin2 mRNA or fragments. More preferably, primers are a pair of primers, having sequences of SEQ ID NO:3 and SEQ ID NO:4, and such primer amplification produces excellent results.

As preferred embodiment of the present invention, reagents are specific anti-βarrestin2 antibodies, antibodies may be monoclonal antibodies or polyclonal antibodies. Antibodies may be produced by using various techniques known to one skilled in the art. For example, purified βarrestin2 proteins can be used in animals (such as rabbits) to induce production of polyclonal antibodies. Similarly, βarrestin2-expressing cells can be used to immunize animals to produce antibodies. Antibodies can also be monoclonal antibodies. This kind of monoclonal antibodies may be prepared by using conventional hybridoma technology.

With regard to designing specific probes for βarrestin2 genes is known to one skilled in the art, for example, preparing a probe, which can specifically bind predetermined position of βarrestin2 gene, but cannot specifically bind genes other than βarrestin2 gene, and, in addition, probes contain detectable signals.

Methods of using antibodies that specifically bind βarrestin2 proteins to determine βarrestin2 protein expression in samples are also known to one skilled in the art. Most commonly used, for example, are Western blot techniques.

The present invention also provides test kits for determining whether or not βarrestin2 is present and its expression levels, test kit contains: reagents that specifically identify βarrestin2 proteins or encoding genes or transcripts. In addition, test kit may further contain various reagents required for isolation of DNA, PCR, hybridization, staining, etc., including but not limited to: isolation solutions, amplification solutions, hybridization solutions, enzymes, control solutions, staining solutions, washing solutions, etc. Furthermore, test kit may also contain user manuals and/or nucleotide sequence analysis software, etc.

I. Materials and Methods

Mice

βarr1-ko and βarr2-ko mice are provided by Dr. Robert J. Lefkowitz (Duke University Medical Center, Durham, N.C.). βarr1-tg and βarr2-tg mice are generated as described (Shi, Y., et al., "*Critical regulation of CD4+ T cell survival and autoimmunity by beta-arrestin 1*," Nature Immunol., 8, 817-24 (2007)). All other mice are from Shanghai Laboratory Animal Center, Chinese Academy of Sciences. Animal experiments are performed in accordance with the National Institutes of Heath Guide for the Care and Use of Laboratory Animals. Mice are fed with a regular diet (Formulab 5008, Labdiet 5053) or high-fat diet (55% fat calories) (Harlan-Teklad 93075) and have free access to water and diet. Adenovirus ($7 \times 10^9$ viral particle/100 μl saline) is injected into the tail vein of db/db mice and C57BL/6 to specifically target the liver. Body weight and food intake are measured as described in: Netea, M. G., et al., "*Deficiency of interleukin-18 in mice leads to hyperphagia, obesity and insulin resistance*," Nature Medicine, 12, 650-6 (2006).

Immunoprecipitation and Immunoblotting

After mouse is sacrificed, mouse tissues are quickly excised and frozen in liquid nitrogen. Tissue lysate is prepared and protein concentration is determined by Bradford method. For immunoprecipitation, add relevant antibodies to cell lysate, incubate at 4° C. overnight, add protein A or protein G agarose beads, incubate at 4° C. for 2 h. Proteins that bind protein A or protein G agarose beads are washed in SDS sample buffer and treated at 50° C. for 20 min followed by SDS-PAGE separation and through immunoblotting method to determine relevant proteins. For immunoblotting, protein bands, emitting infrared fluorescence through excitation of IRDye800CW conjugated secondary antibody, are obtained by Odyssey infrared imaging system, followed by using Scion Image software (Li-Cor Bioscience, Lincoln, Nebr., USA) to perform quantitative analysis. Methods are as described in: Gao, H., et al., "*Identification of beta-arresting as a G protein-coupled receptor-stimulated regulator of NF-kappaB pathways*," Mol. Cell, 14, 303-17 (2004); and Luan, B., et al., "*Beta-arrestin2 functions as a phosphorylation-regulated suppressor of UV-induced NF-kappaB activation*," EMBO J., 24, 4237-46 (2005).

Intraperitoneal Glucose and Insulin Tolerance Tests (GTTs and ITTs)

For GTTs, mice are injected intraperitoneal with glucose after starvation for 6 hours. Blood glucose is measure at indicated time points. Mice are injected intraperitoneally under fed conditions for ITTs. Blood are collected and determined the glycemia using a glucometer (Roche Accu-chek). Serum insulin levels are measured using rat/mouse ELISA kit.

Statistical Analysis

All data are shown as mean±SEM. Measurements at single time points are analyzed by ANOVA or if appropriate by Student's t-test. Time courses are analyzed by repeated-measurements (mixed model) ANOVA with Bonferroni post-tests. P<0.05 indicates significant differences.

Cell Transfection and Plasmids

Human hepatocyte Hep3B cells (purchased from ATCC) are transfected by LipofectAMINE (Invitrogen). For all transfection experiments, CMV-β-Gal is used to compensate the total DNA input. Full length of Akt and Src are cloned into modified pcDNA3 vector in-frame with HA or Flag at the N-terminus. Akt Tyr315/326Ala is also cloned into modified pcDNA3 vector in-frame with Flag at the N-terminus. Plasmids containing cDNA encoding βarrestin2 and its truncation mutants are generated as described in Gao, H., et al., "*Identification of beta-arrestin2 as a G protein-coupled receptor-stimulated regulator of NF-kappaB pathways*," Mol. Cell, 14, 303-17 (2004). The authenticity of the DNA sequences is confirmed by sequencing.

Antibodies

Anti-βarrestins rabbit polyclonal antibody (A1CT and A2CT) is a gift from Dr. Robert J. Lefkowitz (Duke University Medical Center, Durham). Antibodies directed against Akt (total), Akt (phosphorylated Thr308), Akt (phosphorylated Ser473), GSK3-α/β (phosphorylated Ser21/9), Foxo1 (total), Foxo1 (phosphorylated Ser256), Src, phosphorylated Tyr and IR are obtained from Cell Signaling Technology, Inc. (Danvers, Mass., U.S.A.). GSK3-α/β antibody is from Santa Cruz Biotechnology, Inc. (Santa Cruz, Calif., U.S.A.). PP2 and Wortmannin from Sigma-Aldrich (St. Louis, Mo., U.S.A.).

Detection Kits

Rat/mouse insulin ELISA kit is from Linco Research, Inc. (St. Charles, Mo., U.S.A.). PI3-Kinase ELISA kit from Echelon Biosciences, Inc. (Salt Lake City, Utah, U.S.A.) Rat/mouse glucagon ELISA kit, NEFA, Triglycerides, and Cholesterol detection kit from WAKO Chemicals USA (Richmond, Va.). Mouse Epinephrine ELISA kit from USCN Life Science (Wuhan, China). Akt Kinase Assay Kit is from Cell Signaling Technology, Inc.

Adenovirus Preparation and Injection

Adenoviruses encoding Gal, βarrestin2, βarrestin2 1-185 and βarrestin2 186-409 are generated by using adEasy system according to the manufacture's instruction (Stratagene, La Jolla, Calif., U.S.A.). The CsCl purified adenovirus are used as a saline solution ($7 \times 10^9$ virus particles per 100 ml) and injected through tail vein.

Real-Time Quantitative RT-PCR

Real-time quantitative PCR coupled with reverse transcription (RT-PCR) is performed. βarrestin mRNA level are analyzed by real time PCR following reverse transcription as described in Kang, J., et al., "*A nuclear function of beta-arrestin1 in GPCR signaling: regulation of histone acetylation and gene transcription*," Cell, 123, 833-47 (2005). HPRT mRNA levels are used to normalize between samples. The primer pairs used for RT-PCR are: mouse βarrestin1-sense, 5'-AAGGGACACGAGTGTTCAAGA-3' (SEQ ID NO: 1), antisense, 5'-CCC GCT TTC CCA GGT AGA C-3' (SEQ ID NO: 2); mouse βarrestin2-sense, 5'-GGC AAG CGC GAC TTT GTA G-3' (SEQ ID NO: 3), antisense, 5'-GTG AGG GTC ACG AAC ACT TTC-3' (SEQ ID NO: 4); mouse HPRTsense, 5'-CCT GCT GGA TTA CAT TAA AGC ACT G-3' (SEQ ID NO: 5), antisense, 5'-TTC AAC ACT TCG AGA GGT CCT-3' (SEQ ID NO: 6).

Tissue-Specific Glucose Metabolism and Insulin Action

Glucose production in primary hepatocyte was measured as described in Yang, Q., et al., "*Serum retinol binding protein 4 contributes to insulin resistance in obesity and type 2 diabetes*," Nature, 436, 356-62 (2005), and glucose (GO) Assay Kit from Sigma is used to detect glucose concentration. Ex vivo glucose uptake was measured as previously described in Dubois, M. J., et al., "*The SHP-1 protein tyrosine phosphatase negatively modulates glucose homeostasis*," Nature Med. 12, 549-56 (2006), and 2-[$^3$H]-deoxy-D-glucose was from PerkinElmer (Waltham, Mass., U.S.A.).

Primary Hepatocyte Isolation and Culture

Primary hepatocytes are isolated and cultured after perfusion and collagenase digestion of the liver (Arkan, M. C., et al., "*IKK-beta links inflammation to obesity-induced insulin resistance*," Nature Med. 11, 191-8 (2005)).

H/E Staining

Adipose tissue samples are fixed in 4% PFA overnight. Paraffin embedding, sectioning, and H&E staining were performed according to standard protocols.

II. EXAMPLES

Example 1

Downregulation of βarrestin2 in Type 2 Diabetic Mice

In searching for new targets for therapeutic intervention of insulin resistance, inventors of the invention looked for molecules that are differentially expressed in tissues from insulin resistant mice, especially in tissues known to be important in insulin responses. From these studies, it was unexpectedly found that the expression levels of βarrestins are down-regulated in the db/db mouse model of type 2 diabetes in liver, and skeletal muscle, which are important tissues for insulin regulations and functions.

As shown in FIG. 1A, βarrestin2 protein expressions are down-regulated by nearly 50% in liver, and by about 20% in the skeletal muscle of db/db mice. The decreases in βarrestin2 protein expressions are accompanied by the decreases in the mRNA levels. As shown in FIG. 1B, βarrestin2 mRNA levels drop by about 50% in liver and about 20% in skeletal muscle of the db/db mice. Because liver and skeletal muscle are major insulin-sensing tissues, these observations suggest that βarrestin2 may play a role in insulin resistance or the development of insulin-resistant diseases, such as type 2 diabetes.

To further assess the involvement of βarrestin2 in insulin resistance, these experiments are repeated in dietary-induced insulin-resistant mice. Dietary-induced insulin-resistant model mice were generated by a high-fat (55% fat) diet (HFD), as described in Yang, Q. et al., "*Serum Retinol Binding Protein 4 Contributes To Insulin Resistance In Obesity And Type 2 Diabetes*," Nature 436, 356-62 (2005). In these mice, βarrestin2 protein levels were found to decrease by ~60% in liver and by ~30% in skeletal muscle (FIG. 1C). The βarrestin2 mRNA levels are also reduced by ~50% in liver and ~30% in skeletal muscle (FIG. 1D). On the other hand, expression levels of βarrestin2 in adipose tissue (FIGS. 1A-1D), brain (data not shown) or lung (data not shown) of either db/db mice or HFD-induced mice are not changed to any appreciable extent. In addition, βarrestin1 is also slightly down-regulated in liver and skeletal muscle of these insulin-resistant mice (FIG. 1A, FIG. 1B, and data not shown). However, the down-regulation of βarrestin1 is much less than that of βarrestin2, suggesting that βarrestin1 may not play an important role in insulin-related disorders.

Example 2

Downregulation of βarrestin2 in Type 2 Diabetic Patients

In addition to mouse models, the expression levels of βarrestins are also assessed in clinical samples. The protein levels of βarrestins in liver samples from patients with type 2 diabetes (8 pairs) are assessed. FIG. 8A shows that βarrestins are down-regulated in a manner similar to that found in the mouse models.

Together, changes in βarrestins protein and mRNA expression levels in these insulin-resistant mice and clinical samples suggest that βarrestin2 may play a role in insulin signaling, and that dysfunction of these proteins may contribute to insulin resistance and type 2 diabetes. These are indeed found to be the case, as described below.

Example 3

Deficiency of βarrestin2 Contributes to Insulin Resistance

To assess the potential roles of βarrestins in insulin signaling and type 2 diabetes, the involvement of βarrestins in whole body insulin action and glucose metabolism are investigated. βarrestin2 knockout (βarr2-ko) mice were generated. These βarr2-ko mice lack βarrestin2 (FIG. 9A, top bar), but are found to be viable and fertile with normal body weights and food intakes (FIG. 9A), as compared to the wild type littermates. When fasted, the βarr2-ko mice have similar serum insulin levels (FIG. 2A) and blood glucose levels (FIGS. 2B, 2E), as compared to the fasted wild type littermates. However, in re-fed stages, the knockout mice show much higher serum insulin levels (FIG. 2A) and blood glucose levels (FIG. 2B) than those in the wild type littermates, indicating that the βarr2-ko mice have higher demands for insulin and have defects in glucose homeostasis.

Similar results are seen in human patient samples. For example, FIG. 8B shows that patients with down-regulated βarrestin protein levels also have significantly higher blood glucose levels, and these elevated blood glucose levels are seen in the fasting state.

Figure 9:
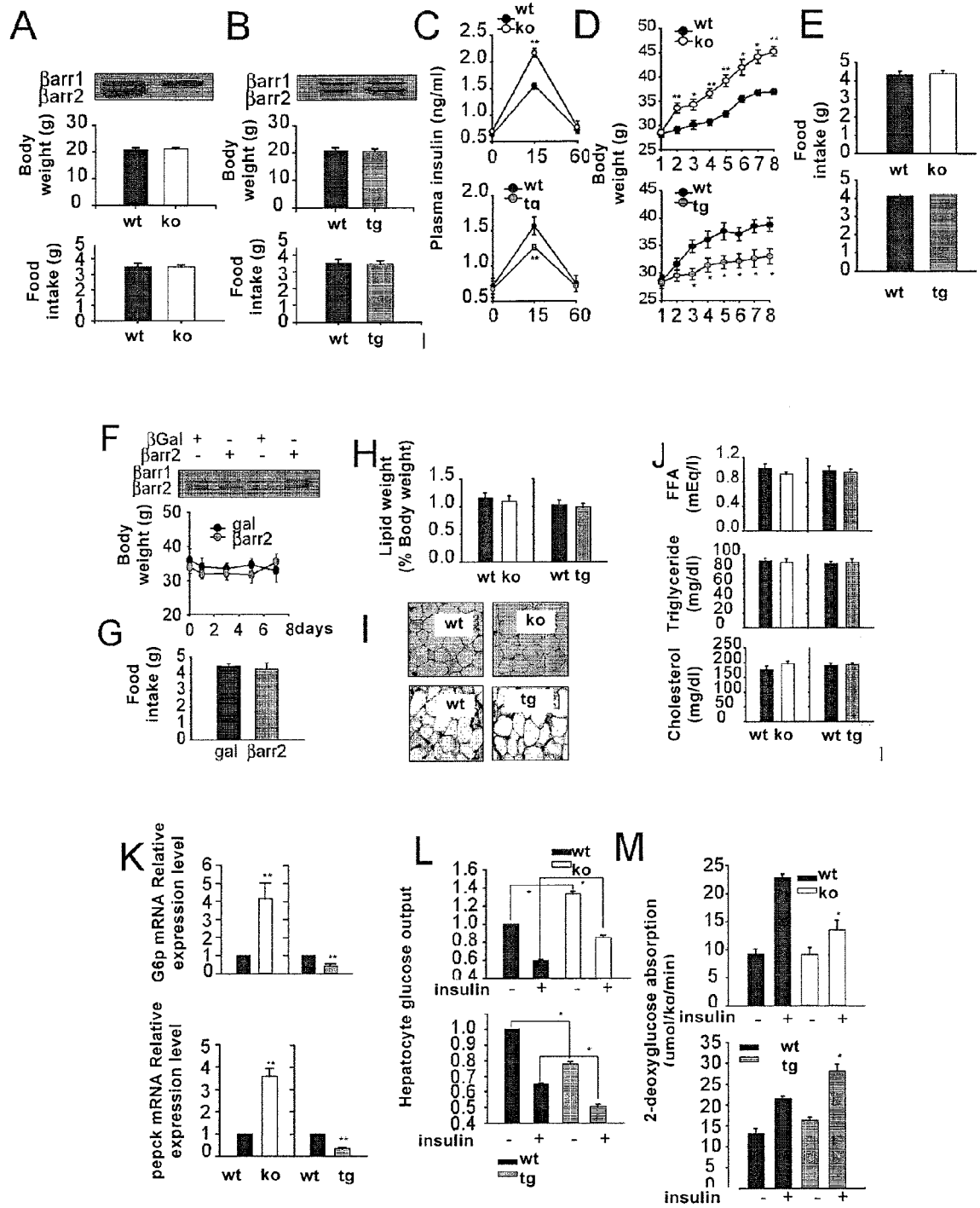
FIGS. 9A-M show βarrestin2 increased insulin sensitivity in liver and muscle.

Because βarrestin2 knockout leads to defects in glucose homeostasis, it was next investigated whether increased arrestin2 expression would have improved insulin action and glucose homeostasis. Transgenic mice expressing human βarrestin2 driven by CMV promoter (βarr2-tg) were generated and found to have a ~2-fold increase in liver βarrestin2 expression, as compared with non-transgenic mice (FIG. 9B; top bar). The βarr2-tg mice develop normally with normal food intake and body weight (FIG. 9B). The serum insulin levels and blood glucose levels of the βarr2-tg mice are similar to those of the wild type mice in the fasted stages (FIGS. 2C, 2D); however, the serum insulin levels and blood glucose levels of the βarr2-tg mice are much lower in the re-fed stages (FIGS. 2C, 2D), suggesting that the βarr2-tg mice have an improved capacity to regulate glucose homeostasis.

Figure 2:
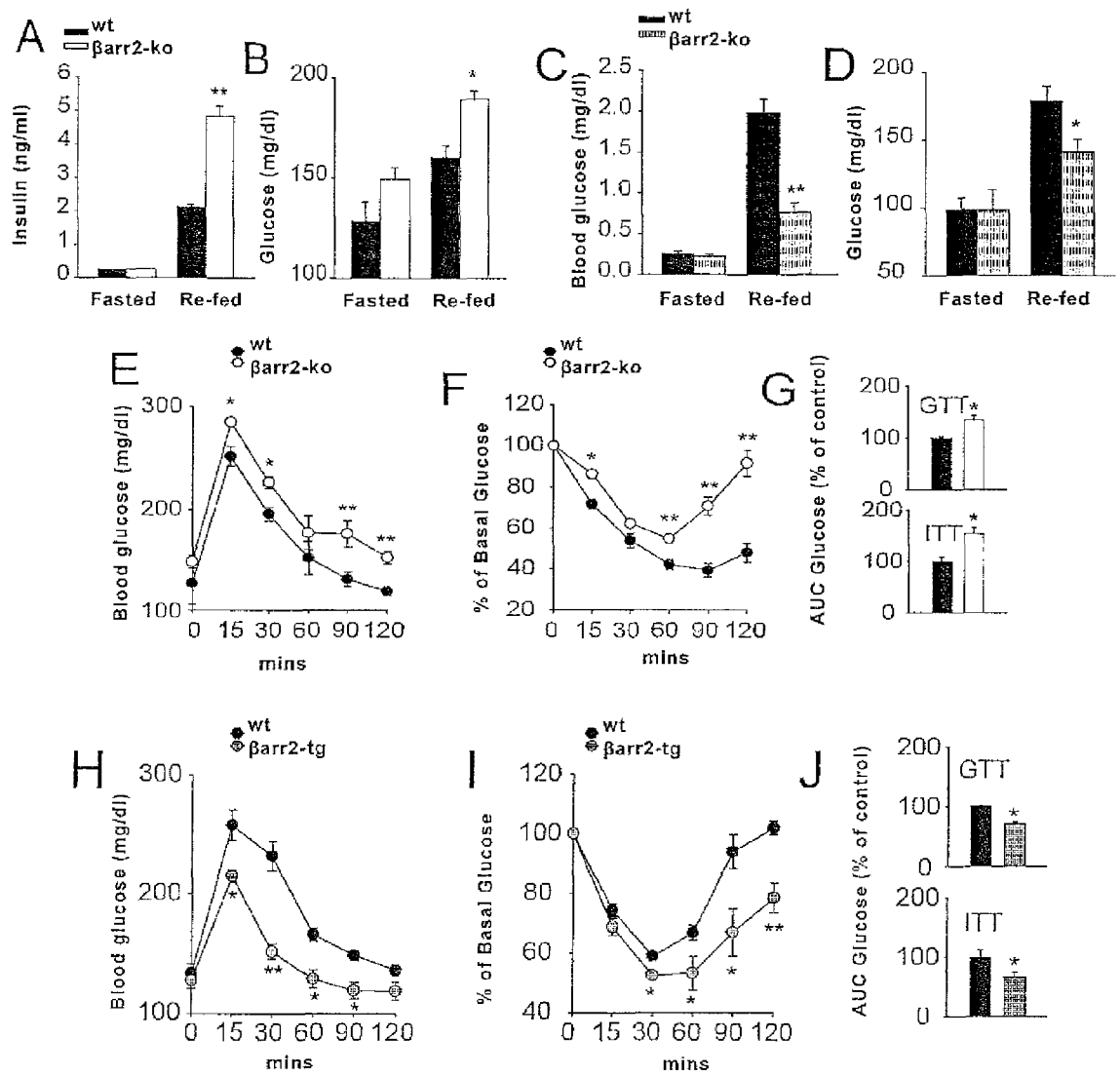
FIGS. 2A-J show deficiency of βarrestin2 leads to insulin resistance. Serum insulin (FIG. 2A) and blood glucose (FIG. 2B) levels in βarr2-ko mice (n=8) and wild type littermates (n=8) under fasted and re-fed stages. Serum insulin (FIG. 2C) and blood glucose (FIG. 2D) levels in βarr2-tg mice (n=8) and wild type littermates (n=8) under fasted and re-fed stages. Glucose levels during GTTs (1 g·kg$^{-1}$) (FIG. 2E) and ITTs (1 U·kg$^{-1}$) (FIG. 2F) in βarr2-ko mice (n=10) and wild type littermates (n=8). Area-under-the-curve (AUC) glucose levels were shown in FIG. 2G. GTTs (1 g·kg$^{-1}$) (FIG. 2H), ITTs (0.75 U·kg$^{-1}$) (FIG. 2I) and AUC glucose levels (FIG. 2J) in βarr2-tg mice (n=11) and wild type littermates (n=8). All mice were 8-weeks old and fed with a regular diet. Data are presented as mean ±s.e.m. *P<0.05, **P<0.005, versus control.

To further define the role of βarrestin2 in whole-body insulin sensitivity, the glucose tolerance tests (GTTs) and insulin tolerance tests (ITTs) are performed on βarr2-ko, βarr2-tg, and their wild type littermates. Intraperitoneal injection with 1 g/kg glucose triggers a rapid increase in blood glucose levels followed by a gradual return to the near fasting levels in 2 hours in the wild type mice. However, in the βarr2-ko mice, a higher blood glucose level was observed after the glucose challenge (FIGS. 2E, 2G). Insulin secretion in response to glucose load during GTTs is also higher in the βarr2-ko mice (FIG. 9C), suggesting deteriorated insulin sensitivity in these knockout mice. This hypothesis is further confirmed by insulin tolerance tests (ITTs) (FIGS. 2F, 2G).

In ITTs, intraperitoneal injection with 1 U·kg$^{-1}$ insulin induces a time-dependent reduction of blood glucose and a gradual return to nearly normal level in both the wild type littermates and the βarr2-ko mice (FIG. 2F). However, the blood glucose reduction is dampened and the hypoglycemic effect of insulin is less sustained in the βarr2-ko mice, as compared to their wild type littermates (FIGS. 2F and 2G). These results indicate that the βarr2-ko mice have reduced insulin sensitivities.

In contrast, the results from GTTs (1 g·kg$^{-1}$) and ITTs (0.75 U·kg$^{-1}$) using βarr2-tg mice show that insulin sensitivities of the βarr2-tg mice are enhanced, as compared with their wild type littermates (FIG. 2H, I, J, and FIG. 9C).

Taken together, these in vivo analyses, using βarr2-ko and βarr2-tg mice, reveal that deficiency in βarrestin2 impairs insulin sensitivity, while elevation of βarrestin2 protein levels improves insulin sensitivity. These results attest to the importance of βarrestin2 in insulin sensitivity and glucose homeostasis.

Liver, skeletal muscle and adipose tissue are major insulin-sensing tissues, and these tissues are involved in the development of insulin resistance and type 2 diabetes. As noted above, there is no significant change in the βarrestin2 levels in adipose tissues (FIGS. 1A-1D). In addition, there is no difference in the white adipose tissue weights, adipocyte sizes, plasma free fatty acids (NEFA), triglycerides, and cholesterols among βarr2-ko mice, βarr2-tg mice, and their wild type littermates (FIG. 9H-J). These results suggest that adipose tissues are not as important as liver or muscle as sites where βarrestin2 regulates insulin actions.

Impaired suppression of hepatic glucose production and decreased muscle glucose uptake are major events of insulin resistance and glucose intolerance. See, Arkan, M. C. et al., "*IKK-beta links inflammation to obesity-induced insulin resistance,*" Nat. Med., 11, 191-8 (2005). Therefore, we compare the hepatic insulin sensitivity of βarr2-ko or βarr2-tg mice with their wild type littermates. Phosphoenolpyruvate carboxykinase (PEPCK) and glucose-6-phosphatase (G6P) are two key gluconeogenic enzymes. The expression levels of these two enzymes are elevated in the liver of βarr2-ko mice under fasted conditions, but are attenuated in the liver of βarr2-tg mice (FIG. 9K). Primary hepatocytes from βarr2-ko mice have increased basal glucose production and impaired suppression of hepatic glucose production in response to insulin (FIG. 9L). Opposite phenomena were observed in βarr2-tg mice (FIG. 9L). All these observations support the notion that βarrestin2 positively contributes to hepatic insulin sensitivity.

Furthermore, basal glucose uptakes in muscles are studied using 2-deoxy-D-[$^3$H]-glucose. In soleus muscles isolated from βarr2-ko mice or βarr2-tg mice, glucose uptakes are similar to that of their wild type littermates. However, insulin-stimulated increases in glucose uptakes are ~2-fold lower in βarr2-ko mice, but ~1.5-fold higher in βarr2-tg mice, as compared to their wild type littermates (FIG. 9M). Similar results are also found in entensor digitorum longus (EDL) muscle (data not shown). These results together indicate that βarrestin2 can positively regulate insulin sensitivity in muscle.

Example 4

Administration of βarrestin2 Restores Insulin Sensitivity

To explore the potential preventive and therapeutic roles of βarrestin2 in obesity-induced insulin resistance, the βarr2-ko, βarr2-tg, and their wild type littermates are challenged with a HFD for 8 weeks. βarr2-ko mice gain about 50% body weight in comparison to a ~30% gain for their wild type littermates, while βarr2-tg mice gained ~10% less body weight than their wild type littermates (FIG. 9D), despite similar food intake of these mice (FIG. 9E). The GTTs (1.5 g·kg$^{-1}$) and ITTs (1.5 U·kg$^{-1}$) results of these HFD-treated mice further confirm that βarrestin2 can promote insulin sensitivity (FIG. 3A-F), thereby alleviates the development of obesity and obesity-induced insulin resistance.

Results from the above described transgenic approach indicate that βarrestin2 can be an effective preventive and therapeutic agent. However, to use βarrestin2 as a preventive or therapeutic agent, βarrestin2 would need to be introduced into cells from exogenous sources—e.g., by delivering the βarrestin2 proteins or expression vectors into the cells. For βarrestin2 protein delivery, liposomes or similar technologies may be use. Such techniques are well known in the art.

To express βarrestin2 in cells, a polynucleotide encoding βarrestin2 may be constructed into an expression vector (e.g., plasmids or viral vectors, such as adenovirus, retrovirus, herpesvirus, vaccinia virus, adeno-associated virus, CMV, SV40, or RSV), wherein the expression of βarrestin2 may be driven by a suitable promoter, such as a general promoter (β-actin promoter) or a tissue-specific promoter (such as a liver, adipose tissue, or skeletal muscle specific promoter). If a viral vector is used, the viruses can infect the cells and express the βarrestin2 protein inside the cells. If the vector is a plasmid, it may be delivered into the cell by using liposomes or similar agents. The use of liposome of similar argents for gene transfection is well known in the art.

Figure 3:
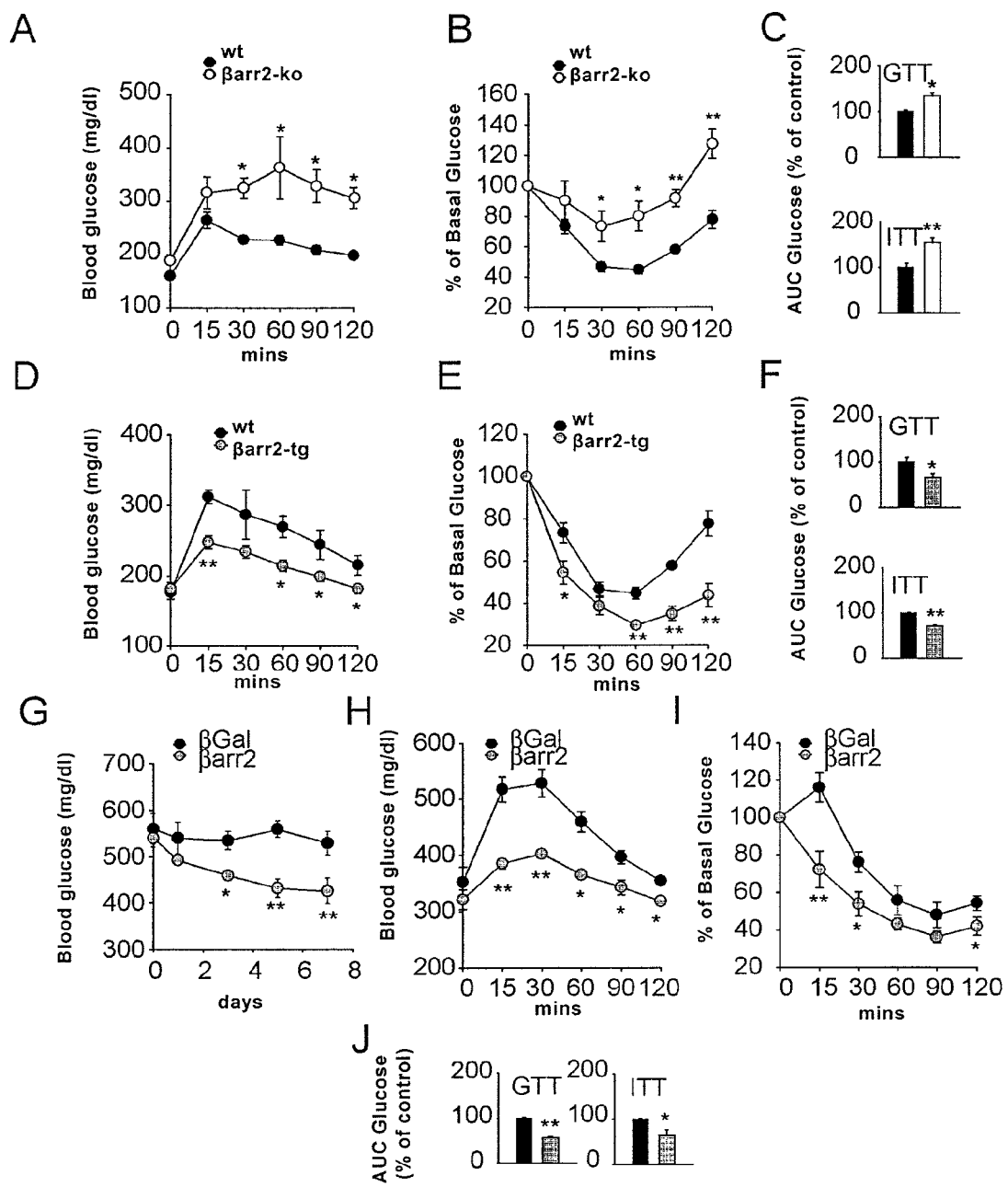
FIGS. 3A-J show administration of βarrestin2 restores insulin sensitivity. GTTs (1.5 g·kg$^{-1}$) (FIG. 3A), ITTs (1.5 U·kg$^{-1}$) (FIG. 3B) and AUC glucose levels (FIG. 3C) in βarr2-ko mice (n=8) and wild type littermates (n=8) fed on HFD for 8 weeks. GTTs (1.5 g·kg$^{-1}$) (FIG. 3D), ITTs (1.5 U·kg$^{-1}$) (FIG. 3E) and AUC glucose levels (FIG. 3F) in βarr2-tg mice (n=8) and wild type littermates (n=8) fed on HFD for 8 weeks.

For example, to evaluate the therapeutic potential of βarrestin2 in preventing or treating insulin resistance and type 2 diabetes, βarrestin2-containing adenoviruses may be administered into the db/db diabetic mice, e.g., by intravenous injection. Administration of such a recombinant adenovirus into the db/db diabetic mice led to a ~3-fold increase in the βarrestin2 protein levels in the liver, without altering the food intakes and body weights (FIGS. 9F and G). The blood glucose levels under fed conditions are reduced in the db/db mice that received the βarrestin2 adenovirus, as compared to the control mice (i.e., mice that received adenoviruses harboring a β-galatosidase gene (βGal)) (FIG. 3G). βarrestin2 adenovirus injection also ameliorates glucose tolerance and insulin tolerance in GTTs (1.5 g·kg$^{-1}$) and ITTs (1.5 U·kg$^{-1}$) (FIGS. 3H-J).

These results demonstrate that increasing βarrestin2 expression not only improves insulin sensitivity in normal mice and prevents obesity-induced insulin resistance, but also restores insulin sensitivity in type 2 diabetic mice, suggesting a novel preventative and therapeutic strategy based on βarrestin2 for insulin resistance and type 2 diabetes.

Example 5

βarrestin2 Promotes Akt Activation Through Scaffolding Akt/Src Interaction

In order to fully explore the therapeutic potential of βarrestin2, we investigated the molecular mechanisms of the βarrestin2 actions. At the molecular level, insulin resistance results from defects in insulin signaling in peripheral tissues. To understand how βarrestin2 mediates insulin sensitivity, the insulin signaling events in liver and skeletal muscle of βarr2-ko mice and βarr2-tg mice are compared to those in the normal mice.

Figure 4:
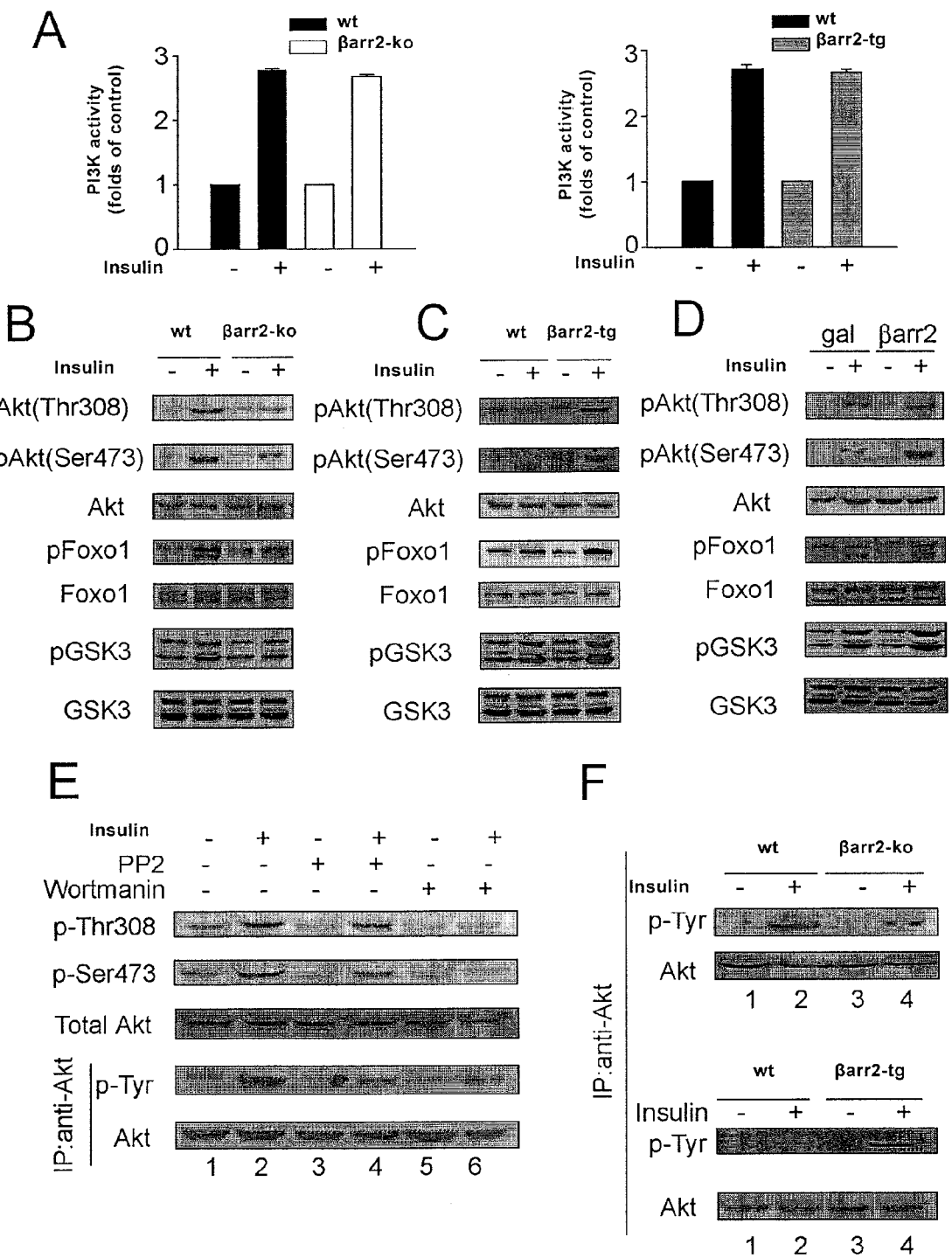
FIGS. 4A-F show βarrestin2 promotes Src-dependent Akt activation by insulin-stimulation.
Figure 10:
FIGS. 10A-G show βarrestin2 increased insulin signaling in liver and muscle.

FIG. 4A shows that insulin stimulation leads to a ~3-fold increase in PI3K activity in liver of wild type, βarr2-ko and βarr2-tg mice. That activation of PI3K by insulin is similar in mice of all genotypes suggests that βarrestin2 is not directly involved in the activation of PI3K. In contrast, different activities of Akt are induced by insulin in livers of βarr2-ko and wild type mice, as monitored by in vitro kinase assay (e.g., phosphorylation of GSK3 to pGSK3) (FIG. 10A). Further, FIGS. 4B and 10B show that insulin stimulation results in a ~3-fold increase in the phosphorylation of Akt at Thr308 or Ser473 in liver of wild type mice, whereas such increase is reduced by 50% in βarr2-ko mice. In contrast, insulin-stimulated Akt T308/S473 phosphorylation is increased by ~2-fold in liver of βarr2-tg mice (FIGS. 4C and 10B). Similar results is also found in skeletal muscle of βarr2-ko mice and βarr2-tg mice (FIGS. 10F, and G). Accordingly, the phosphorylation levels of GSK3 (3 and Foxo1 by Akt is attenuated in liver of βarr2-ko mice, but enhanced in βarr2-tg mice, as compared to those in the wild type mice (FIGS. 4B, and C).

In addition to the above results based on transgenic approach, exogenously introduced βarrestin2 proteins are also found to have similar effects. Specifically, βarrestin2 adenovirus injection into db/db mice caused a ~2-fold increase in Akt T308/S473 phosphorylation, as well as GSK3 13 and Foxo1 phosphorylation, in liver following insulin stimulation (FIGS. 4D, and 10C). Thus, the adenoviral expression vector containing the βarrestin2 coding sequence is effective in enhancing the expression levels of βarrestin2 in cells, and βarrestin2 thus expressed are functional. Accordingly, such expression vectors can be effective preventive and therapeutic agents.

The results described above indicate that βarrestin2 can promote insulin stimulated phosphorylation and activation of Akt, but not the PI3K activity. This observation suggests that βarrestin2 mediated functions may be downstream of PI3K.

Akt activation is tightly regulated by PI3K activity. Recent studies show that phosphorylation of Akt at Tyr315/326 by Src enhances Akt serine/threonine phosphorylation and is a prerequisite for full Akt activation. Consistent with that idea, tyrosine and serine/threonine phosphorylation of Akt are remarkably reduced in Hep3B hepatocytes in the presence of Src inhibitor PP2 (FIG. 4E). In addition, Akt activity is reduced when Tyr315/326 of Akt is mutated to Ala, which abolishes Tyr phosphorylation of Akt by Src (FIG. 10E). On the other hand, both serine/threonine phosphorylation and tyrosine phosphorylation of Akt are abolished in Hep3B hepatocytes by Wortmannin, a PI3K inhibitor, thus, supporting the view that Akt and Src are both downstream of PI3K (FIG. 4E).

To understand how βarrestin2 mediates its function without relying on PI3K, tyrosine phosphorylations of Akt in liver of βarr-ko and βarr2-tg mice, as compared to the wild type mice, are examined. Insulin-stimulation led to a ~2-fold increase in tyrosine phosphorylation of Akt in the wild type mice (FIG. 4F, upper panel, lane 2 vs. lane 1, and FIG. 10D), which is reduced by ~40% in βarr2-ko mice (lane 4 vs. lane 2) and increased by ~1.5-fold in βarr2-tg mice (FIG. 4F, lower panel, lane 4 vs. lane 2, and FIG. 10D). Together, these results suggest that βarrestin2 may enhance the Src-mediated phosphorylation of Akt at tyrosine residues and may consequently promote Akt serine/threonine phosphorylation and activation.

Figure 5:
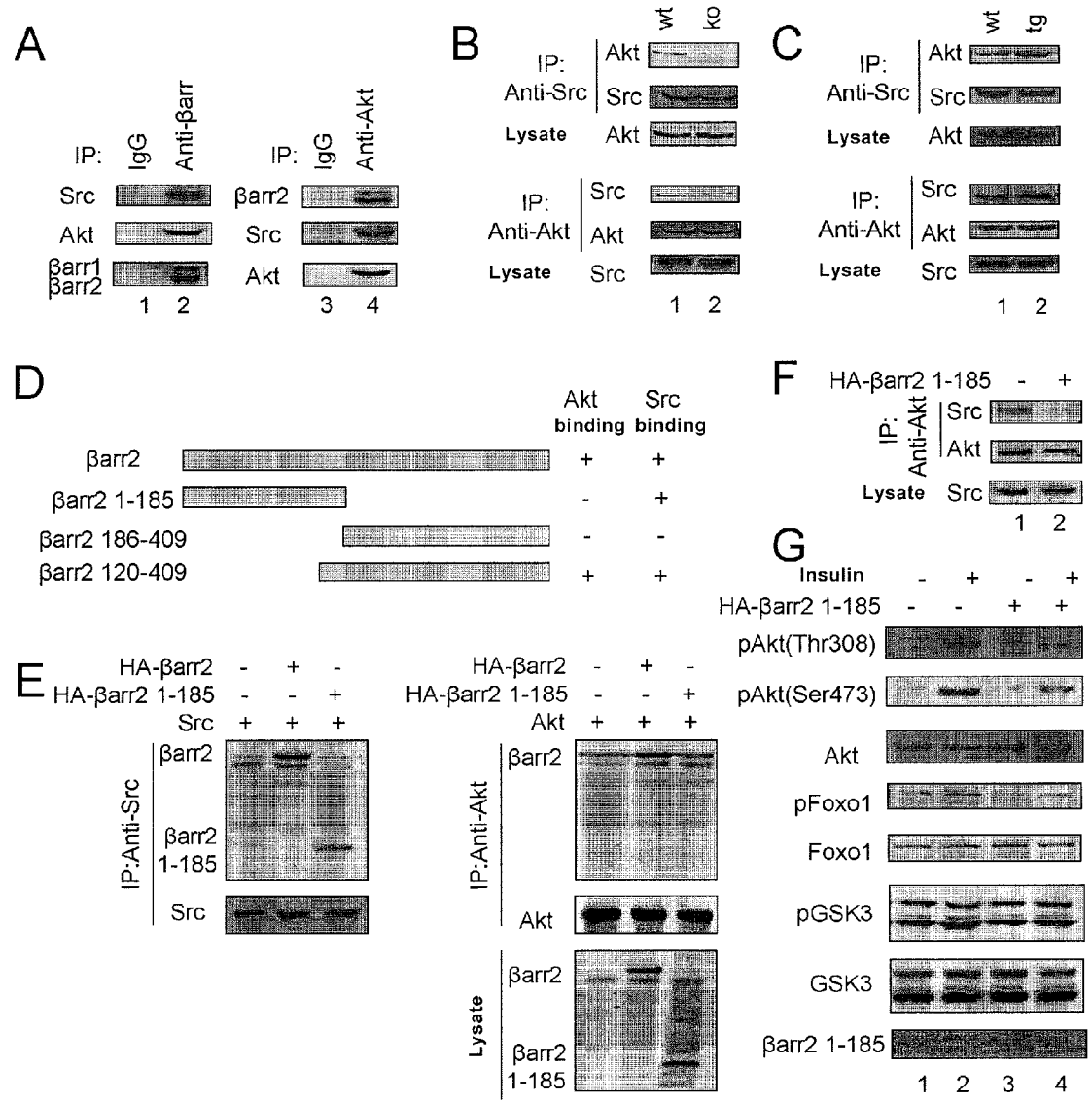
FIGS. 5A-G show scaffolding of Akt/Src interaction by βarrestin2.

It is known that βarrestins can function as adaptors to promote the activation of various mitogen-activated protein kinases, such as ERK1/2 and JNK3. A similar scaffolding mechanism may also exist in the context of βarrestin2-mediated insulin signaling. To test this possibility, the interactions between Akt, βarrestin2, and Src in C57BL/6 mice livers are examined. FIG. 5A shows that considerable amounts of endogenous Src and Akt are co-immunoprecipitated with endogenous βarrestin2 (lane 2). The interactions among Akt, βarrestin2, and Src, are also observed when the immunoprecipitation is performed using anti-Akt antibodies (FIG. 5A, lane 4) in C57BL/6 mice livers lysates. These results support the notion that Akt, βarrestin2, and Src form a complex in vivo.

To further verify the scaffolding function of βarrestin2 in the putative Akt/βarrestin2/Src complex, immunoprecipitations using liver samples from βarr2-ko mice, βarr2-tg mice, and wild type littermates are performed. Livers of all groups of mice show similar expression levels of Akt and Src (FIGS. 5B, and C). Interestingly, the association between Src and Akt is dramatically reduced in mice lacking βarrestin2 (FIG. 5B, lane 2 vs. lane 1, and FIG. 11A). Conversely, Akt and Src interaction is remarkably enhanced in βarr2-tg mice (FIG. 5C and FIG. 11B). These results indicate that βarrestin2 is essential in mediating the association between Akt and Src in vivo.

To determine the regions of βarrestin2 that interact with Akt and Src, a series of truncation mutants of βarrestin2 are generated and analyzed in the immunoprecipitation assays (FIG. 5D). Deletion of the N-terminus (amino acids 1-185) or the C-terminus (amino acids 185-409) of βarrestin2 results in complete loss of βarrestin2 binding to Akt, while deletion of N-terminal amino acids 1-119 does not affect βarrestin2-Akt interactions (FIG. 11C). Thus, at least one of the regions spanning amino acids 120-185, amino acids 185-409, and amino acids 120-409 of βarrestin2 is necessary for βarrestin2 binding with Akt.

As for Src, deletion of βarrestin2 N-terminus (amino acids 1-185) results in a loss of Src binding. Conversely, a βarrestin2 fragment, spanning amino acids 1-185, interacts with Src as efficiently as does wild type βarrestin2. This results indicates that Src binds to the N-terminus of βarrestin2, and the binding site is within the region of amino acids 1-185 of βarrestin2.

The above results suggest that βarrestin2 region spanning amino acids 1-185 may only interact with Src but not Akt (FIG. 5E). Therefore, a truncated form of βarrestin2 containing amino acids 1-185 (βarrestin2 1-185) is used to verify the requisite of βarrestin2 for Src-dependent activation of Akt in insulin signaling. When overexpressed in Hep3B hepatocytes, βarrestin2 1-185 inhibits Akt/Src interactions, presumably by competing with the endogenous βarrestin2 (FIG. 5F, lane 2 vs. lane 1). Meanwhile, the insulin-stimulated phosphorylations of Akt, GSK3P, and Foxo1 are markedly reduced in the presence of βarrestin2 1-185, (FIG. 5G, lane 4 vs. lane 2). Thus, βarrestin2 1-185 may act as a dominant negative mutant to disrupt the Akt/Src complex, thereby inhibiting the insulin-stimulated activation of Akt. These data demonstrate the pivotal role of βarrestin2 in scaffolding the Akt/βarrestin2/Src complex that may promote Src-dependent Akt activation in insulin signaling.

Example 6

βArrestin2 Links Akt/Src to Insulin-Activated IR

Figure 6:
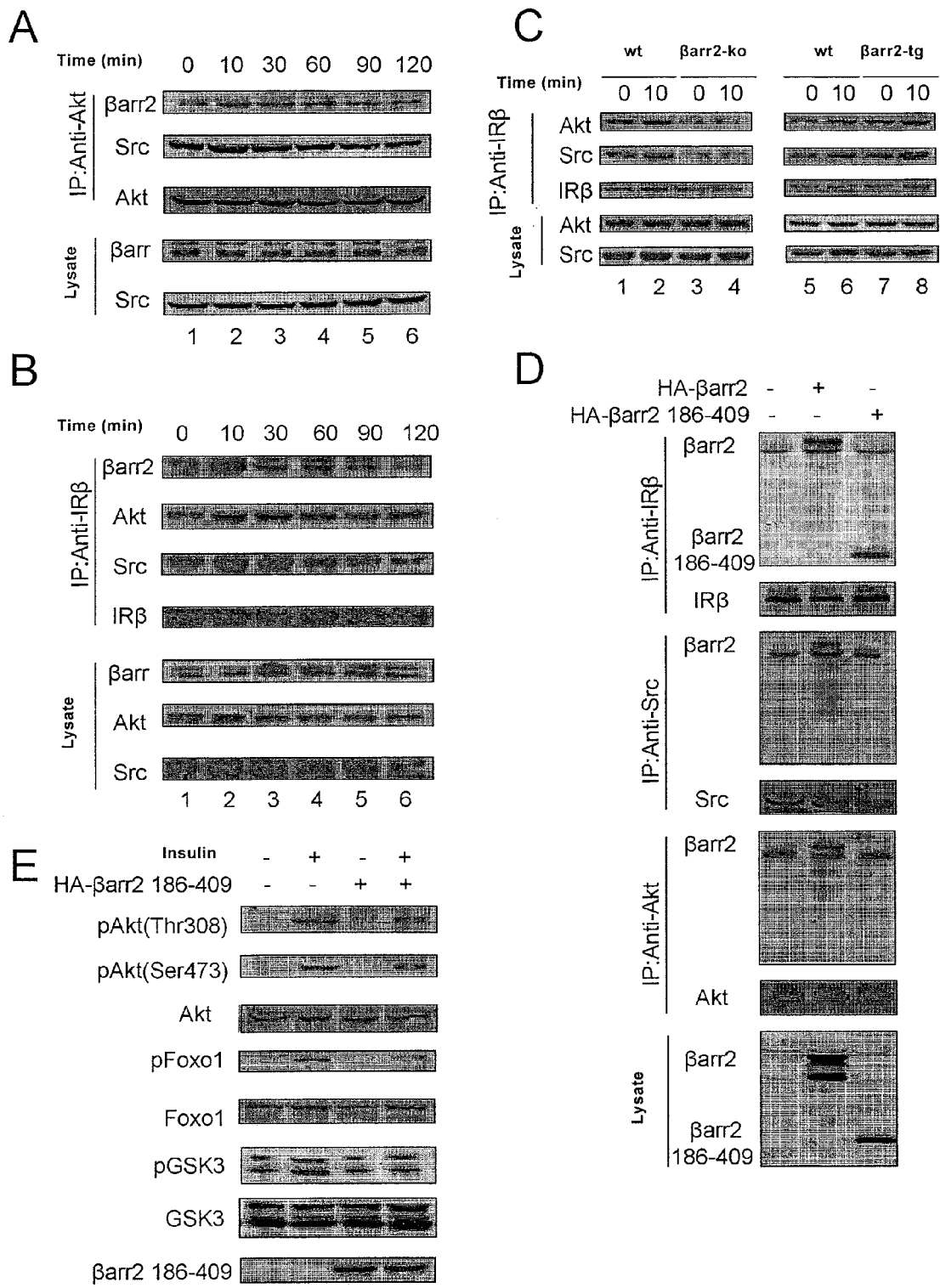
FIGS. 6A-E show insulin stimulated the formation of Receptor/Akt/βarrestin2/Src signal complex.
Figure 12:
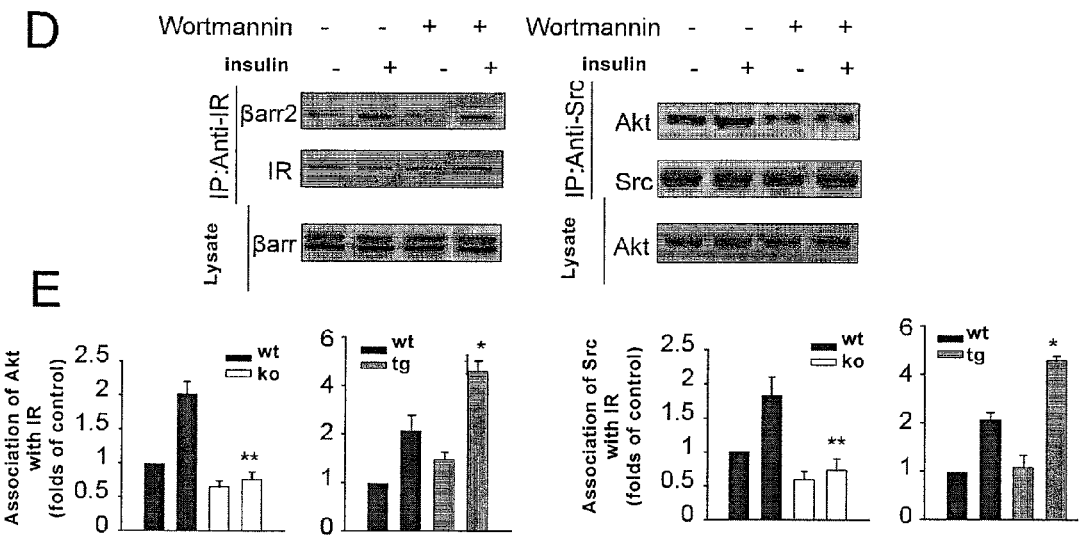
FIGS. 12A-E show insulin stimulated the formation of Receptor/Akt/βarrestin2/Src signal complex.

The observation that βarrestin2 plays a pivotal role in scaffolding the Akt/βarrestin2/Src complex suggests that this complex formation may have a role in insulin stimulation. To test this possibility, the formation of this complex in response to insulin stimulation is examined. FIG. 6A and FIG. 12B show intraperitoneal administration of insulin triggers a marked increase of Akt/Src interactions as well as Akt/βarrestin2 association in a time-dependent manner in C57BL/6 mice livers, suggesting that insulin-stimulation indeed promotes the formation of the Akt/βarrestin2/Src protein complex.

That the formation of the Akt/βarrestin2/Src protein complex is stimulated by insulin suggests that this complex or one of its component may interact directly with the insulin receptor. Indeed, direct interactions between βarrestin2 and IR in vitro are observed (FIG. 12A). Further immunoprecipitation of IR reveals a time-dependent recruitment of βarrestin2 to the receptor (FIG. 6B and FIG. 12C). Interaction between βarrestin2 and IR is insensitive to Wortmannin-treatment (FIG. 12D), demonstrating that this interaction is independent of PI3K.

Associations of Akt and Src with IR also change in a manner similar to that of βarrestin2 association with IR (FIG. 6B, and FIG. 12C). Associations of Akt and Src with IR are normally mediated by PI3K (FIG. 12D). Moreover, association of Akt and Src with IR is unexpected to also depend on expression level of βarrestin2 (FIG. 6C), indicating that βarrestin2 may be essential for association of Akt/Src with IR. Importantly, overexpression of βarrestin2 186-409, a truncated mutant that interacts with IR but not Akt or Src (FIG. 6D) in Hep3B hepatocytes, suppresses the insulin stimulated Akt activation (FIG. 6E), thus functioning as a dominant negative mutant. These results indicate that βarrestin2 can mediate the formation of an active IR/Akt/βarrestin2/Src signaling complex following insulin stimulation.

Example 7

Figure 7:
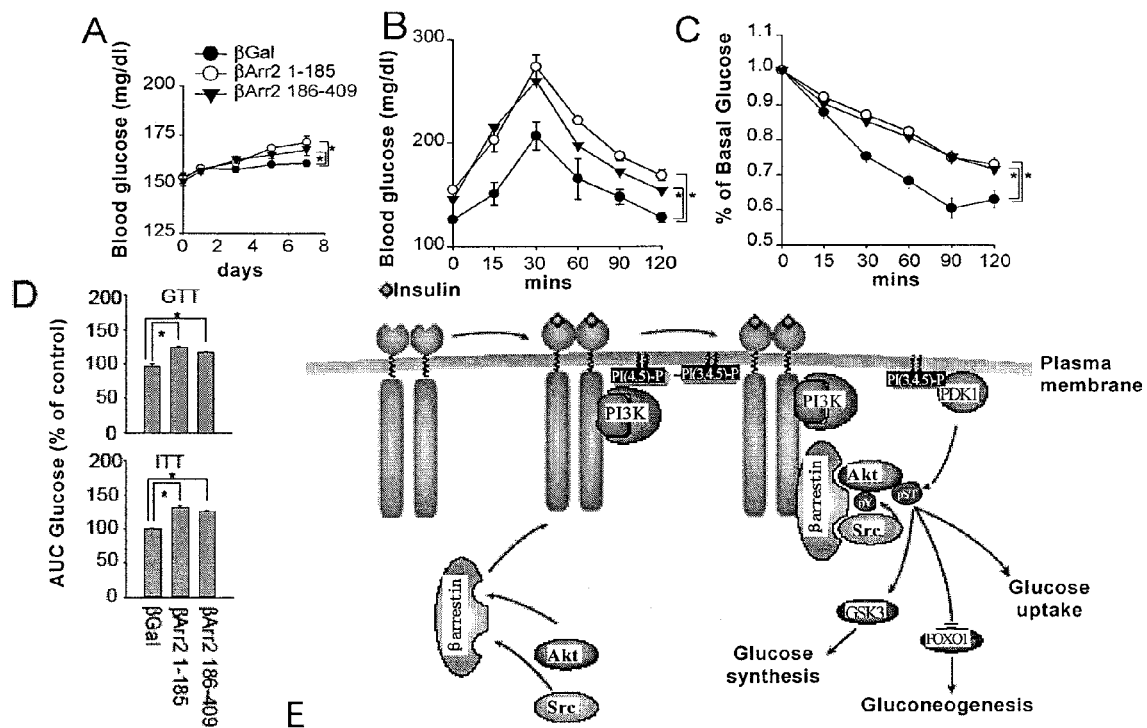
FIGS. 7A-E show expression of βarrestin2 1-185 or 186-409 mutants contributes insulin resistance.
Figure 13:
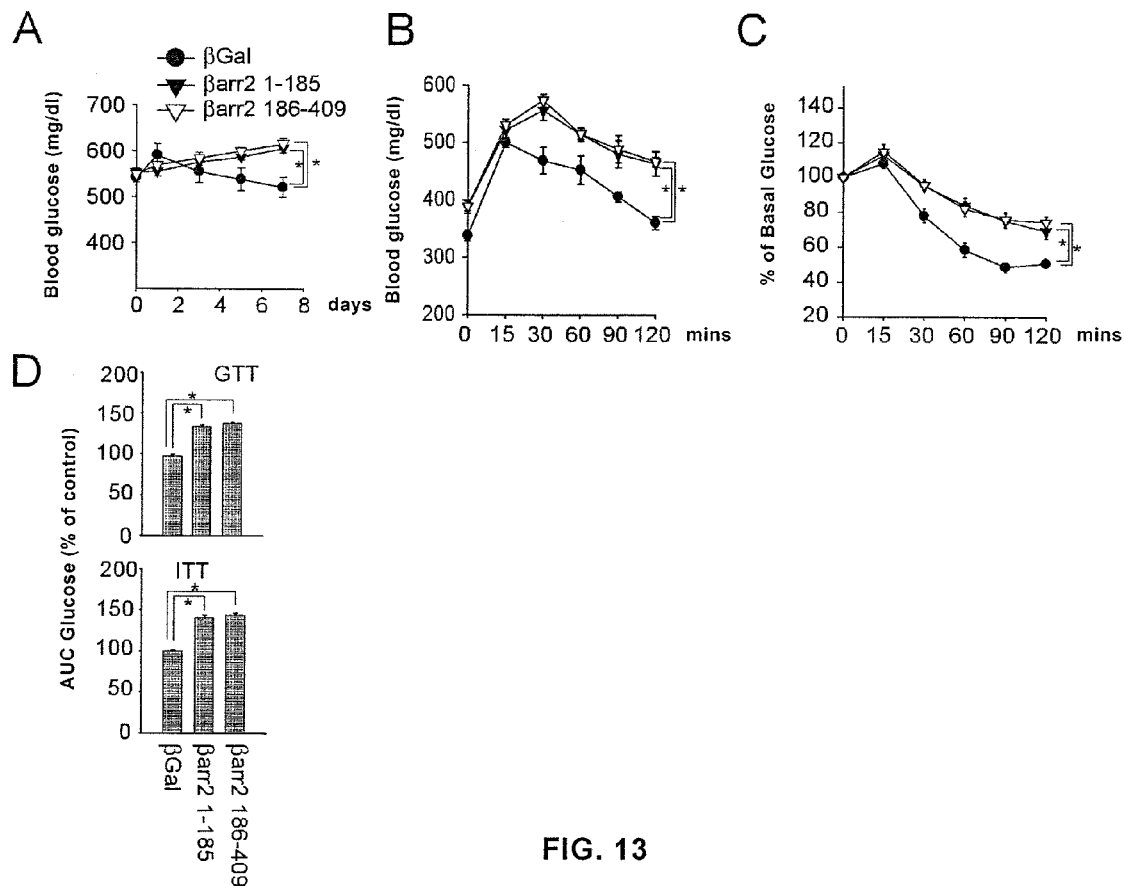
FIGS. 13A-D show expression of βarrestin2 1-185 or 186-409 mutants aggravates insulin resistance in db/db mice.

Expression of βarrestin2 1-185 or 186-409 Mutants may Contribute to Insulin Resistance In Vivo βarrestin2 1-185 and βarrestin2 186-409 both function in a dominant negative fashion to inhibit insulin-stimulated Akt activation. It is possible that expression of these two mutants may contribute to insulin resistance in vivo. To test this possibility, adenovirus encoding βGal, βarrestin2 1-185 and βarrestin2 186-409 are injected intravenously into C57BL/6 mice and db/db diabetic mice. C57BL/6 mice infected with βarrestin2 1-185 and βarrestin2 186-409 adenovirus show higher blood glucose levels than that of the control mice at all time points (FIG. 7A). βarrestin2 1-185 and βarrestin2 186-409 adenovirus injections also impair glucose tolerance and insulin tolerance as shown in GTTs (1 g·kg$^{-1}$) and ITTs (1 U·kg$^{-1}$) (FIG. 7B-D). Similar results are also obtained in db/db diabetic mice (FIG. 13). These results indicate that βarrestin2 mutants that are capable of disrupting the IR/Akt/βarrestin2/Src signal complex may aggravate insulin insensitivity, thus, contributing to diabetic progression.

Taken together, the above results demonstrate that, upon insulin-stimulation, βarrestin2 may function as a scaffold for Akt/Src interaction and subsequently link the Akt/Src complex to IR forming a signal complex. βarrestin2 appears to function as an indispensable scaffold in this signal complex because knockdown or dysfunction of βarrestin2 results in disruption of this signal complex, insulin signaling, and eventually insulin metabolic action. Thus, the insulin-stimulated IR/Akt/βarrestin2/Src complex formation may be critical for insulin signaling and insulin sensitivity. It is conceivable that deficiency or defect in this complex may contribute to the pathophysiology of insulin resistance and type 2 diabetes.

βarrestins are abundantly expressed in liver and skeletal muscle. However, little is known about the involvement of βarrestins in insulin signaling, as well as their roles in insulin resistance and type 2 diabetes. Inventors of the present invention unexpectedly disclosed a previously unidentified IR/Akt/βarrestin2/Src signal complex that is essential for proper insulin signaling and whole body insulin action. In this signal complex, βarrestin2 functions as scaffolds for the binding of Akt and Src with IR upon insulin-stimulation. Downregulation of βarrestin2 expression or mutation of βarrestin2 leads to disruption of Akt/Src interactions, Src-dependent Akt activation, and insulin actions, thereby boosting insulin resistance and type 2 diabetes traits in vivo. Therefore, these observations indicate a direct physiological relevance of βarrestin2 in the pathophysiology of insulin resistance and type 2 diabetes.

Insulin signaling results in the recruitment of adaptor proteins, such as IRS, GAP, Grb2, and Shc, to insulin receptor. Subsequent activation of IR intrinsic receptor tyrosine kinase activity leads to a cascade of events, such as receptor autophosphorylation, phosphorylation of adaptor proteins like IRS, recruitment and activation of PI3K via interaction of the SH2 domain of PI3K to phosphorylated tyrosine residues on IR, and eventually activation of Akt.

In contrast to the above-described pathway, βarrestin2 mediates the activation of Akt through Src but does not affect PI3K. These two pathways, however, may not be necessarily separated. For example, βarrestin2 may not influence PI3K activity, but it may facilitate the membrane translocation of Akt which would promote Akt activation. βarrestin2 may be essential for the Src-dependent Akt activation by insulin stimulation. Phosphorylation of Akt at tyrosine residues by Src may assist Akt membrane translocation as well as subsequent serine/threonine phosphorylation by upstream kinases PDKs. It is also possible that IRS, PI3K, and PDKs may form in the same signal complex, thus, integrating these two pathways into one signaling network for efficient signal transduction (FIG. 7E).

In cultured fibroblasts, βarrestin1, but not βarrestin2, binds to the ligand-occupied IGF-1 receptors, promotes their endocytosis, and enhances IGF-1-dependent mitogen-activated protein kinase phosphorylation and DNA synthesis (Dalle, S., et al., "*Insulin and insulin-like growth factor I receptors utilize different G protein signaling components*," J. Biol. Chem. 276, 15688-95 (2001); Lin, F. T., et al., "*beta-arrestins regulate mitogenic signaling and clathrin-mediated endocytosis of the insulin-like growth factor I receptor*," J. Biol. Chem., 273, 31640-3 (1998)). However, neither glucose metabolic action nor mitogenic signaling by insulin is dependent on βarrestin1. As noted in this description, βarrestin2, but not βarrestin1, can participate in insulin signaling as well as downstream glucose metabolic actions. These differences between βarrestin1 and βarrestin2 may result from their different binding affinity with Akt.

A weak interaction between βarrestin1 and Akt is observed (FIG. 5A). In contrast, βarrestin2 interacts robustly with Akt both in vitro and in vivo (FIG. 5A). Thus, βarrestin1 and βarrestin2 may, respectively, regulate IGF and insulin signaling pathways, representing their harmonious but non-redundant roles.

The signaling mechanism described here requires the formation of a protein signal complex comprising IR, Akt, Src, and βarrestin2, in which βarrestin2 brings all the components together. A common property of signal complexes is that removal of distinct components in a signal complex yields similar phenotypes. Given the importance of IR, Akt and Src in insulin signaling and in insulin resistance and type 2 diabetes, βarrestin2 plays a critical role in the metabolic disorder, by affecting the signal complex property. For example, mutation or loss of βarrestin2 would result in deficiency of this signal complex, which would then lead to severe insulin resistance and contribute to type 2 diabetes. Consistent with this notion, data from mouse models and clinical samples of type 2 diabetes patients show downregulation of βarrestin2, but not Akt or Src (data not shown). Importantly, administration of βarrestin2 restores insulin sensitivity and ameliorates the symptom of type 2 diabetes in diabetic mice, indicating βarrestin2 may serve as a novel therapeutic agent for preventing or treating type 2 diabetes. These observations support the idea that βarrestin2 may play a central role in this signal complex and may be used as a diagnostic marker or a preventive or therapeutic agent for insulin resistance or type 2 diabetes.

For example, a diagnostic kit containing an antibody recognizing the βarrestin2 protein may be used to detect the expression levels of βarrestin2 in biopsies obtained from, but not limited to liver, adipose tissues, or skeletal muscle, using a variety of protein detection methods, such as immunoblotting, immunoprecipitation, immunohistochemistry staining, or immunofluorescent staining. Alternatively, a diagnostic kit may contain one or more RT-PCR primers that specifically amplify the βarrestin2 mRNA isolated from biopsies obtained from, but not limited to liver, adipose tissues, or skeletal muscle. The mRNA expression levels may be quantified by using detection methods, such as real-time RT-PCR and electrophoresis followed by densitometry analysis. Reduced expression levels of βarrestin2 protein and/or mRNA, as compared with the normal expression levels, would indicate that the patients may have insulin resistance, and thus, becoming candidates for the βarrestin2 or other therapy.

IR signaling is conventionally believed to involve adaptor proteins such as IRS, GAP, Grb2, and Shc, which mediate the formation of signal complexes. On the other hand, βarrestin-mediated signal complexes are believed to be limited to GPCRs. Inventors of the present invention have unexpectedly discovered that βarrestin2 may also participate in IR signaling through scaffolding an IR/Akt/βarrestin2/Src signal complex. Moreover, the formation of this protein complex depends on the stimulation of IR by insulin, suggesting that this complex plays a role in insulin action. Thus, the βarrestin2-mediated signal complex is a newly-discovered, novel intrinsic component of IR signaling and presents a novel target for the diagnosis, prevention, and treatment of insulin resistance and the associated symptoms (such as type 2 diabetes).

As shown above, the β-arrestin2-mediated IR/Akt/β-arrestin2/Src signaling complex plays a critical role in insulin signaling and maintenance of whole body insulin sensitivity. The β-arrestin2-mediated IR/Akt/β-arrestin2/Src signaling pathway thus represents an alternative pathway to insulin-dependent Akt activation. Accordingly, β-arrestin2 presents an attractive target for the diagnosis, prevention, and treatment of insulin resistance and its associated disorders.

Based on these unexpected findings, some embodiments of the invention relate to diagnosis of insulin resistance based on β-arrestin2. In accordance with embodiments of the invention, a sample (e.g., a biopsy specimen from muscle or liver) from a subject is assay for the expression levels of β-arrestin2. The assays may be performed with an antibody (either a polyclonal or monoclonal antibody) and compared to results from a normal subject. An alternative is to use RT-PCT to quantify the mRNA levels in the samples. Antibodies and PCT primers that can be used for these assays are described in the following section, Specific Examples and Experimental Methods Section.

If the expression level of β-arrestin2 is below that of the normal subject, then the subject may have insulin resistance or may be prone to development of insulin resistance. Such subject will be potential patients for the prevention and treatment of insulin resistance based on β-arrestin2 intervention, as described below.

Some embodiments of the invention relate to reagents and methods for the prevention and treatment of insulin resistance and its associated disorders. Reagents in accordance with embodiments of the invention may include an expression vector that contains a sequence encoding β-arrestin2. The vector may be a plasmid type or viral vector. The viral vector may be a retrovirus, adenovirus, herpesvirus, vaccinia virus, or adeno-associated virus. The expression vector may contain a promoter selected from the group consisting of CMV promoter, SV40 promoter, RSV promoter, β-actin promoter, and a tissue-specific promoter. The tissue-specific promoter may be adipose tissue-specific, muscle-specific, or liver-specific.

With plasmid vectors, such vectors may be used with liposomes or similar technologies for delivery to cells. With viral vectors, the virus will infect the cells and therefore no other transfection reagent is needed.

These reagents may be administered to a subject to prevent or treat insulin resistance and the associated disorders. Typically, an effective amount of the reagent may be administered by any suitable routes, such as oral administration, topical application, injection, etc., to the subject. The subject is a mammal, typically a human. The effective amount is the amount needed to produce the desired effect. The techniques for determination of the amounts and administration frequency to achieve the desired effects are well known to one skilled in the art and need not be elaborated. Typically, a practitioner will determine the doses needed based on the weights, ages, physical conditions, dosing regimen, and other considerations.

Advantages of embodiments of the invention may include one or more of the following. The newly discovered β-arrestin2-mediated IR/Akt/β-arrestin2/Src signaling pathway represents an alternative pathway to insulin-dependent Akt activation. β-arrestin2 plays a critical role in the regulation of this pathway with respect to insulin action. Therefore, detection of the expression levels or activities of β-arrestin2 provides a convenient diagnosis of insulin resistance. Similarly, reagents that can be used to increase β-arrestin2 expression in cells (e.g., plasmid-liposome complese, or adenovirus containing sequences encoding β-arrestin2) may be used to prevent or treat insulin resistance and its associated disorders. Preventing or treating insulin resistance using methods or reagents of the invention can be very effective in preventing diabetes or similar disorders because these reagents act on the β-arrestin2-mediate pathway, which can be remedy prior to the development of any symptoms.

While the invention has been described with respect to a limited number of embodiments, those skilled in the art, having benefit of this disclosure, will appreciate that other modifications or variations are possible without departing from the scope of the attached claims.

What is claimed is:

1. A method for treating insulin resistance or an insulin resistance-associated disease in a mammal, comprising administering to the mammal a composition comprising a full-length βarrestin2 protein or an expression vector having a polynucleotide encoding the full-length βarrestin2 protein, wherein the insulin resistance-associated disease is selected from the group consisting of type II diabetes, obesity, hyperinsulinaemia, and glucose intolerance.

2. The method of claim 1, characterized in that the expression vector is a plasmid vector.

3. The method of claim 1, characterized in that the expression vector is a viral vector.

4. The method of claim 3, characterized in that the viral vector is selected from the group consisting of retrovirus, adenovirus, herpes virus, vaccinia virus, and adeno-associated virus.

5. The method of claim 1, characterized in that the mammal is a human.

* * * * *